United States Patent
Klausen et al.

(10) Patent No.: US 9,872,892 B2
(45) Date of Patent: Jan. 23, 2018

(54) ANIMAL FEED ENZYMES

(71) Applicant: Novozymes A/S, Bagsvaerd (DK)

(72) Inventors: Mikkel Klausen, Copenhagen (DK); Klaus Skaalum Lassen, Kastrup (DK)

(73) Assignee: Novozymes A/S, Bagsvaerd (DK)

( * ) Notice: Subject to any disclaimer, the term of this patent is extended or adjusted under 35 U.S.C. 154(b) by 36 days.

(21) Appl. No.: 14/779,121

(22) PCT Filed: May 8, 2014

(86) PCT No.: PCT/EP2014/059449
§ 371 (c)(1),
(2) Date: Sep. 22, 2015

(87) PCT Pub. No.: WO2014/180953
PCT Pub. Date: Nov. 13, 2014

(65) Prior Publication Data
US 2016/0051636 A1    Feb. 25, 2016

(30) Foreign Application Priority Data

May 8, 2013 (EP) .................... 13166956

(51) Int. Cl.
| | |
|---|---|
| *A61K 38/44* | (2006.01) |
| *A61K 45/06* | (2006.01) |
| *A23K 10/30* | (2016.01) |
| *A23K 20/174* | (2016.01) |
| *A23K 20/142* | (2016.01) |
| *A23K 20/189* | (2016.01) |
| *A23K 10/14* | (2016.01) |
| *A23K 20/195* | (2016.01) |
| *A23K 20/20* | (2016.01) |
| *A23K 50/75* | (2016.01) |

(52) U.S. Cl.
CPC ............ *A61K 38/443* (2013.01); *A23K 10/14* (2016.05); *A23K 10/30* (2016.05); *A23K 20/142* (2016.05); *A23K 20/174* (2016.05); *A23K 20/189* (2016.05); *A23K 20/195* (2016.05); *A23K 20/20* (2016.05); *A23K 50/75* (2016.05); *A61K 38/44* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,930,028 A * | 12/1975 | Ullmann | A23C 21/02 210/611 |
| 4,320,116 A | 3/1982 | Bjorck | |
| 4,726,948 A | 2/1988 | Prieels | |
| 5,310,541 A | 5/1994 | Montgomery | |
| 5,389,369 A | 2/1995 | Allen | |
| 5,747,078 A | 5/1998 | De Jong | |
| 2002/0006652 A1 | 1/2002 | Danielsen | |
| 2002/0119136 A1 | 8/2002 | Johansen | |
| 2011/0229598 A1 | 9/2011 | Musser | |
| 2013/0058910 A1 * | 3/2013 | Koepsel | A62D 3/02 424/94.2 |

FOREIGN PATENT DOCUMENTS

| | | |
|---|---|---|
| EP | 1068871 A1 | 1/2001 |
| EP | 2510944 A1 | 10/2012 |
| EP | 2540307 A1 | 1/2013 |
| WO | 91/11105 A1 | 8/1991 |
| WO | 95/27046 A1 | 10/1995 |
| WO | 00/21381 A1 | 4/2000 |
| WO | 2009/137697 A1 | 11/2009 |
| WO | 2013/009910 A2 | 1/2013 |

OTHER PUBLICATIONS

Bernardeau et al., International Journal of Food Microbiology, vol. 77, pp. 19-27 (2002).
Huyghebart et al., The Veterinary Journal, vol. 187, pp. 182-188 (2011).
Jones et al., Poultry Science, vol. 83, pp. 384-391 (2004).
Mikkelsen et al., Pig News and Information, vol. 21, pp. 59-66 (2000).

* cited by examiner

*Primary Examiner* — Vera Afremova
(74) *Attorney, Agent, or Firm* — Elias Lambiris

(57) ABSTRACT

The present invention relates to methods of controlling the growth of microorganisms in animals and animal feed. In particular, the present invention relates to a method of controlling the growth of microorganisms in animals with an antimicrobial composition, the treatment of animal feed with an antimicrobial additive and antimicrobial compositions.

12 Claims, 1 Drawing Sheet

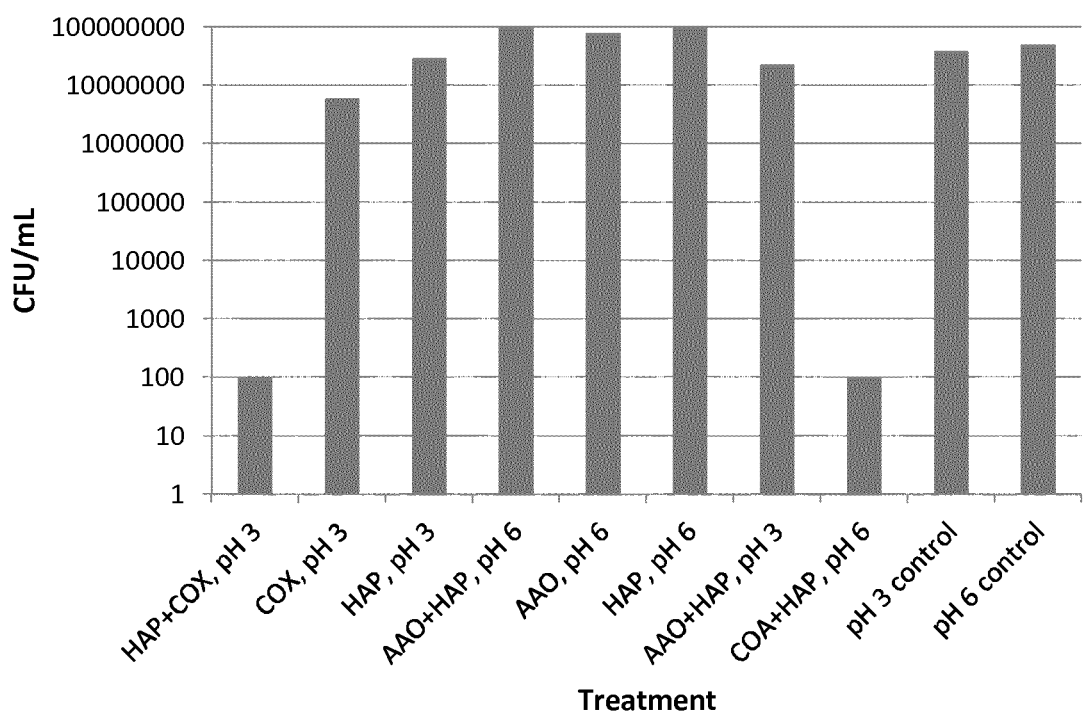

ANIMAL FEED ENZYMES

CROSS-REFERENCE TO RELATED APPLICATIONS

This application is a 35 U.S.C. 371 national application of PCT/EP2014/059449 filed May 8, 2014, which claims priority or the benefit under 35 U.S.C. 119 of European application nos. 13166956.6 filed May 8, 2013. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to methods of controlling the growth of microorganisms in animals and animal feed. In particular, the present invention relates to a method of controlling the growth of microorganisms in animals with an antimicrobial composition, the treatment of animal feed with an antimicrobial additive and antimicrobial compositions.

Background of the Invention

In modern animal farming, various methods have been explored to improve animal health and growth performance. These include better husbandry management, better nutrition and the utilization of feed additives. The most common feed additives used are antibiotics, probiotics, enzymes and organic acids (Bernardeau, M., J. P. Vernoux and M. Gueguen, (2002), "Safety and efficacy of probiotic lactobacilli in promoting growth in post-weaning Swiss mice", *Int J. Food Microbiol.* 77:19-27).

However, extensive use of antibiotics in feed may cause animals to become resistant to antibiotics used to treat bacterial infections in animals as well as humans (Mikkelsen L. L., Jensen B. B., (2000), "Effects of fermented liquid feed on the activity and composition of the microbiodata in the gut of pigs", *Pig News Inform.* 21:59N-66N). This led to a ban of marketing and use of antibiotics as growth promoters in feed by the European Commission on Jan. 1 2006. Consumer pressure in other countries such as the US is pushing animal production to phase out use of antibiotics as growth promoters. Removal of antimicrobial growth promoters from animal feed has sparked the interest for identifying new non-therapeutic alternatives with microbial growth modulating effects in order to sustain a healthy animal intestinal microflora (Huyghebart, Ducatelle and Immerseel, (2011), *Veterinary J.*, 187:182-188).

One source of pathogenic bacteria in animal production is contaminated animal feed. Animal feed is normally heat treated to kill harmful bacteria and pathogens. However, incomplete heat treatment can result in 10-15% of *Salmonella* remaining, and/or incorrect storage of animal feed can further result in feed contaminated with bacteria (see F. T. Jones, 2011, *Poult. Sci.* 83:384-391 for a general review). When the animal eats the contaminated feed, the animal can become infected with the bacteria which eventually can end up with the consumer buying contaminated food in the supermarket. The use of organic acids, often blended with formaldehyde, has been used to control the amount of *Salmonella* in feed after the pelleting process. However, formaldehyde can give regulatory issues and organic acids alone often need several days at inclusion rates of 1% to destroy existing bacteria. These high levels of acids may be costly, be corrosive to milling and feeding equipment and have adverse effects with feed palatability and the availability of vitamins to animals.

Description of the Related Art

U.S. Pat. No. 4,320,116 describes the use of an antibacterial system capable of being activated in the gastrointestinal tract of an animal comprising a lactoperoxidase, a thiocyanate and a water soluble peroxide donor such as an alkali percarbonate or alkali perodide. U.S. Pat. No. 5,389,369 describes the use of a haloperoxidase and an antimicrobial activity enhancing agent, such as an alpha-amino acid, for killing or inhibiting the growth of yeast of sporular microorganisms in the treatment of human or animal subjects and in vitro disinfection applications.

WO00/21381 describes the use of two antimicrobial enzymes, such as a lysozyme and an oxidase, together with an enhancer, such as a polyunsaturated fatty acid, to improve growth and feed conversion ratio (FCR) in for example poultry, pigs and cows.

U.S. Pat. No. 5,747,078 describes a method for the long term preservation of food products, such as cheese, comprising an oxidoreductase that generates hydrogen peroxide from a substrate and a lactoperoxidase. U.S. Pat. No. 5,310,541 describes an animal chew which contains an oxidoreductase and corresponding substrate (such as glucose oxidase and glucose) that generates an antimicrobial agent on being chewed to help prevent e.g. cavies and periodontal diseases in animals.

US2002/0119136 describes a method of killing or inhibiting a microorganisms e.g. in laundry, on hard surfaces, on human skin or in oral care, comprising contacting said microorganism with a composition containing a peroxidase, hydrogen peroxide or a source of hydrogen peroxides such as glucose oxidase/glucose, and a enhancing agent such as a phenothiazine derivative or a syringate derivative. U.S. Pat. No. 4,726,948 describes an anti-bacterial composition capable of being activated in the GI tract of mammals comprising Lactoferrin, a lactoperoxidase and an activating system such as glucose/glucose oxidase.

US2011/229598 discloses an antimicrobial milk product comprising a lactoperoxidase, a glucose oxidase, glucose and an oxidizable agent for feeding to calves. EP1068871 describes an antimicrobial feed complement for calves or toothpaste for pets comprising a lactoperoxidase, a glucose oxidase, glucose, thiocyanate, Lactoferrin, lysozyme, immunoglobulin's and growth factors. EP2510944 discloses an antimicrobial feed complement for cows comprising a lactoperoxidase or chloroperoxidase, a glucose oxidase, iodide, and either glucose or a beta-galactosidase.

SUMMARY OF THE INVENTION

In one aspect, the invention relates to a method of controlling the growth of microorganism in an animal comprising feeding the animal with an antimicrobial composition comprising lactose oxidase and vanadium haloperoxidase. In a second aspect, the invention relates to a method for the treatment of animal feed comprising mixing the animal feed with one or more lactose oxidases and one or more vanadium haloperoxidases. In a third aspect, the invention relates to the use of a composition comprising lactose oxidase and vanadium haloperoxidase to control the growth of microorganisms in an animal. In the fourth aspect, the invention relates to an antimicrobial composition comprising one or more lactose oxidases and one or more vanadium haloperoxidases together with one or more vitamins and/or one or more minerals to control the growth of microorganisms in an animal. In a fifth aspect the invention relates to a method for preparing an animal feed composition.

Overview of Sequence Listing

SEQ ID NO: 1 is the amino acid sequence of a lactose oxidase from *Microdochium nivale* CBS 100236.

SEQ ID NO: 2 is the amino acid sequence of a vanadium haloperoxidase from *Curvularia verruculosa* CBS 147.63.

SEQ ID NO: 3 is the amino acid sequence of a vanadium haloperoxidase from *Curvularia inequalis* CBS 102.42

SEQ ID NO: 4 is the amino acid sequence of an amino acid oxidase from *Trichoderma harzianum* CBS 223.93.

SEQ ID NO: 5 is the amino acid sequence of a vanadium haloperoxidase from *Dreschlera hartlebii*.

SEQ ID NO: 6 is the amino acid sequence of a vanadium haloperoxidase from *Dendryphiella salina*.

SEQ ID NO: 7 is the amino acid sequence of a vanadium haloperoxidase from *Phaeotrichoconis crotalariae*.

SEQ ID NO: 8 is the amino acid sequence of a vanadium haloperoxidase from *Geniculosporium* sp.

BRIEF DESCRIPTION OF THE FIGURES

FIG. 1 shows the number of surviving *E. coli* K12 after treatment at pH 3 or pH 6 with a lactose oxidase (COX), a vanadium haloperoxidase (HAP) and/or an amino acid oxidase (AAO).

DEFINITIONS

Amino Acid Oxidase Activity: The term 'amino acid oxidase activity' is defined herein as enzyme activity that catalyses the reaction of an amino acid, water and oxygen to the corresponding alpha-keto acid, peroxide and ammonium ion. For purposes of the present invention, amino acid oxidase activity may be determined as follows. Pipette into cuvettes Worthington Peroxidase (0.01 ml of 10 mg/ml aqueous solution) and 0.2 M triethanolamine buffer pH 7.6 containing 0.1% L-leucine and 0.0065% o-dianisidine (2.9 ml). Incubate in spectrophotometer at 25° C. for 4-5 minutes to achieve temperature equilibration and record blank. Add 0.1 ml of enzyme at a concentration of 0.05-0.2 units per millilitre and record increase in absorbance at 436 nm for 4-5 minutes. Calculate $\Delta A436$ from the initial linear portion of the slope. Activity=units/mg=$(\Delta A436 \times 3.0 \times dilution)/(8.1 \times 0.1 \times (mg/ml))$.

Animal: The term "animal" includes all animals. In one embodiment, the term "animal" excludes humans. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include pet animals, e.g. horses, cats and dogs; mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn), calves (young ruminant without functional rumen or with developing rumen). Preferred animals are mono-gastric animals, preferably poultry and swine (as defined herein).

Antimicrobial composition: The term "antimicrobial composition" means a polypeptide or a chemical composition which has antimicrobial activity.

Antimicrobial activity or antimicrobial effect: The term "antimicrobial activity" or "antimicrobial effect" means the capability of killing and/or inhibiting the growth of microbial cells. Examples of microbial cells are cells of microorganisms. Antimicrobial activity may, e.g., bactericidal and/or a bacteriostatic and/or fungicidal and/or fungistatic and/or virucidal.

Bactericidal: The term "bactericidal" means an agent that is capable of killing bacterial cells. Bactericidal activity is measured as a logarithmic reduction (log reduction) in the number of living cells or Colony Forming Units per mL (CFU/mL), e.g. 1 log reduction corresponds to a reduction in the number of living cells of *Escherichia coli* K12 or *Enterococcus faecalis* DSM2570 from $Y \times 10^X$ CFU/M (CFU: Colony Forming Units; M: mL or g) to $Y \times 10^{X-1}$ CFU/M, where X can be 1, 2, 3, 4, 5, 6, 7, 8, 9, 10 or 11, and Y can be any number from 0 to 10. The number of living cells is determined as the number of *E. coli* or *E. faecalis*, respectively, which can grow on Tryptone Soya Agar (#CM129, Oxoid, England) plates at 30° C.

Bacteriostatic: The term "bacteriostatic" means being capable of inhibiting bacterial growth, i.e. inhibiting the growth of bacterial cells.

Carbohydrate oxidase activity: The term "carbohydrate oxidase activity" is defined herein as enzyme activity that catalyses the oxidation of the primary alcohol in various mono- or oligosaccharides accompanied by reduction of molecular oxygen to hydrogen peroxide. For purposes of the present invention, carbohydrase oxidase activity is determined according to the procedure described by Blake et al. (1989) *Analytical Biochemistry* 177: 156-160. One unit of carbohydrate oxidase activity equals the amount of enzyme capable of releasing 1 μmole of hydrogen peroxide per minute at pH 6.0, 25 degree Celsius. Lactose oxidase activity can also be determined using this method, but wherein lactose is used as substrate.

Controlling the growth of microorganisms: The term "controlling the growth of microorganisms" means that the microorganism is either killed or inhibited, such that the microorganisms are in a non-growing state, i.e., that they are not able to propagate. Controlling the growth of microorganisms further means that there is a change in the intestinal microflora composition of the animal to a microflora composition that is beneficial to the animal, beneficial to animal performance, beneficial to feed utilization (such as FCR) and/or limits the growth of pathogens in the digestive system of the animal.

Fungicidal: The term "fungicidal" means being capable of killing fungal cells.

Fungistatic: The term "fungistatic" means being capable of inhibiting fungal growth, i.e. inhibiting the growth of fungal cells.

Gastric Stable: The term "gastric stable" means that the enzyme(s) are stable to the conditions found in the gastrointestinal tract of an animal, or representative in vitro conditions as defined herein, such that the enzyme(s) can reduce CFU count by at least 10 fold, such as at least 100 fold, at least 500 fold or at least 1000 fold after such a treatment. For the purpose of the present invention, gastric stability was determined using simulated gastric juices, as described in example 2. In summary, the enzyme(s) were incubated with 0.001 M HCl, 35 nM NaCl and 1.1 unit pepsin/mL at 40° C. for 15 minutes and the antimicrobial activity was then tested. The enzymes(s) are classed as gastric stable if they reduce CFU count by at least 10 fold after such a treatment compared to a control sample whereby the enzyme(s) have not undergone incubation with the simulated gastric juices.

Gut: The term "gut" means the gastrointestinal or digestive tract (also referred to as the alimentary canal) of an animal, and refers to the system of organs including the esophagus, stomach, small intestine (including duodenum, jejunum and ileum) and large intestine (including caecum, colon and rectum) within multicellular animals which takes in food, digests it to extract energy and nutrients, and excretes the remaining waste. The microflora of the gut refers to the natural microbial cultures residing in the gut which maintain the good health of an animal by aiding in proper digestion and/or supporting immune system functions.

Haloperoxidase Activity: The term 'haloperoxidase activity' is defined herein as enzyme activity that catalyses the oxidation of halides (e.g. Cl—, Br—, or I—) in the presence of hydrogen peroxide to the corresponding hypohalous acid. For purposes of the present invention, haloperoxidase activity may be determined by mixing 100 µL of haloperoxidase sample (about 0.2 µg/mL) and 100 µL of 0.3 M sodium phosphate pH 7 buffer-0.5 M potassium bromide-0.008% phenol red, adding the solution to 10 µL of 0.3% $H_2O_2$, and measuring the absorption at 595 nm as a function of time.

An alternative assay using monochlorodimedone (Sigma M4632, $\epsilon=20000$ $M^{-1}$ $cm^{-1}$ at 290 nm) as a substrate may be carried out by measuring the decrease in absorption at 290 nm as a function of time. The assay is done in an aqueous solution of 0.1 M sodium phosphate or 0.1 M sodium acetate, 50 µM monochlorodimedone, 10 mM KBr/KCl, 1 mM $H_2O_2$ and about 1 µg/mL haloperoxidase. One haloperoxidase unit (HU) is defined as 1 micromol of monochlorodimedone chlorinated or brominated per minute at pH 5 and 30° C.

Microorganism: The term "microorganism" include bacteria, protozoa, algae, fungi (including yeast), and virus.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the –nobrief option) is used as the percent identity and is calculated as follows:

(Identical Residues×100)/(Length of Alignment–
Total Number of Gaps in Alignment)

Virucidal: The term "virucidal" means being capable of inactivating or killing viruses.

DETAILED DESCRIPTION OF THE INVENTION

In jurisdictions where subject matter concerning treatment of the animal or human body is considered to be un-patentable or an exception to patentability, then said subject matter is herein disclaimed throughout the entire application.

We have surprisingly found that an antimicrobial composition comprising lactose oxidase and vanadium haloperoxidase is highly effective at controlling the growth of microorganisms which, for example, reside in contaminated animal feed. Whilst antimicrobial compositions comprising a lactoperoxidase/myeloperoxidase and glucose oxidase are known in the art, the combination of a lactose oxidase and vanadium haloperoxidase has not previously been shown to have antimicrobial properties, at least for conditions relevant for use as animal feed. Furthermore, the lactoperoxidase/myeloperoxidase and glucose oxidase solutions known from the art need to incorporate substrates (e.g. glucose for glucose oxidase or thiocyanate/bromide/chloride for lactoperoxidase) into the formulation for the enzymes to have an antimicrobial effect.

The inventors have surprisingly shown that the antimicrobial composition of the invention works without the requirement that the substrates for the enzymes are added into the composition. Instead, the enzymes can utilise the required substrate directly from a broad range of feed stocks which are used in animal feed, thereby reducing the cost of the feed for the farmer.

Methods of Controlling the Growth of Microorganisms in an Animal

In a first aspect, the present invention provides a method of controlling the growth of microorganisms in an animal, comprising feeding the animal with an antimicrobial composition comprising a lactose oxidase and a vanadium haloperoxidase. In an embodiment, the method of controlling the growth of microorganisms comprising feeding an animal that is not human with an antimicrobial composition comprising a lactose oxidase and a vanadium haloperoxidase. In one aspect, controlling the growth of microorganisms with the antimicrobial composition of the invention occurs in the gut of the animal.

In an embodiment, the lactose oxidase and vanadium haloperoxidase are gastric stable. The antimicrobial composition of the invention may also comprise one or more sources of halide, hydrogen peroxide and/or one or more sources of hydrogen peroxide, such as cellobiose, lactose, maltose, and/or raffinose. In another aspect, the antimicrobial composition of the invention further comprises forage, concentrates, vitamins, minerals, amino acids, enzymes and/or other feed ingredients, as defined herein The method for controlling the growth of microorganisms in an animal may be carried out with an effective amount of the antimicrobial composition of the invention, wherein an effective amount is the amount suitable for obtaining the required antimicrobial effect in the chosen application. In one aspect, the method of controlling the growth of microorganisms in an animal comprises feeding the animal with an antimicrobial composition of the invention that inhibits the growth of microbial cells, e.g. the antimicrobial composition is a bacteriostatic.

In another embodiment, the method of controlling the growth of microorganisms in an animal comprises feeding the animal with an antimicrobial composition of the invention that kills the growth of microbial cells, e.g. the antimicrobial composition is bactericidal. In a preferred embodiment, the method of controlling the growth of microorganisms in an animal comprises feeding the animal with an antimicrobial composition of the invention that kills at least 90%, such as at least 99%, at least 99.5%, at least 99.7%, at least 99.9%, at least 99.95%, at least 99.97%, at least 99.99% of the number of bacterium, wherein the bacterium is from the genus *Salmonella, Escherichia, Campylobacter, Listeria* and/or *Clostridium*, preferably from *Escherichia*, more preferably from *E. Coli*, even more preferably from *E. Coli* K12.

In another embodiment, the method of controlling the growth of microorganisms in an animal comprises feeding the animal an animal feed comprising one or more lactose oxidases of the invention and one or more vanadium haloperoxidases of the invention together with one or more vitamins and/or one or more minerals. A preferred embodiment is animal feed containing no Lactoferrin.

In a further embodiment, the method of controlling the growth of microorganisms in an animal comprises feeding the animal an antimicrobial composition of the invention, wherein the antimicrobial composition is a component of animal feed. The animal feed may further comprise one or more vitamins and/or one or more minerals. A preferred embodiment is animal feed containing no Lactoferrin.

In a further embodiment, the lactose oxidase is the polypeptide of SEQ ID NO: 1 and the vanadium haloperoxidase is the polypeptide of SEQ ID NO: 2. In a further embodiment, the lactose oxidase is the polypeptide of SEQ ID NO: 1 and the vanadium haloperoxidase is the polypeptide of SEQ ID NO: 3. In a further embodiment, the lactose oxidase is the polypeptide of SEQ ID NO: 1 and the vanadium haloperoxidase is the polypeptide of SEQ ID NO: 5. In a further embodiment, the lactose oxidase is the polypeptide of SEQ ID NO: 1 and the vanadium haloperoxidase is the polypeptide of SEQ ID NO: 6. In a further embodiment, the lactose oxidase is the polypeptide of SEQ ID NO: 1 and the vanadium haloperoxidase is the polypeptide of SEQ ID NO: 7. In a further embodiment, the lactose oxidase is the polypeptide of SEQ ID NO: 1 and the vanadium haloperoxidase is the polypeptide of SEQ ID NO: 8.

Use of Compositions to Control the Growth of Microorganisms in Animals

Another aspect of the invention is the use of a composition comprising a lactose oxidase and a vanadium haloperoxidase to control the growth of microorganisms in an animal. In an embodiment, the use of a composition comprising a lactose oxidase and a vanadium haloperoxidase to control the growth of microorganisms is in an animal that is not human. In an embodiment, the lactose oxidase and vanadium haloperoxidase are gastric stable.

The composition may also comprise one or more sources of halide, hydrogen peroxide and/or one or more sources of hydrogen peroxide, such as cellobiose, lactose, maltose, and/or raffinose. In another aspect, the antimicrobial composition of the invention further comprises forage, concentrates, vitamins, minerals, amino acids, enzymes and/or other feed ingredients, as defined herein.

The use of a composition comprising a lactose oxidase and a vanadium haloperoxidase to control the growth of microorganisms in an animal may be carried out with an effective amount of the composition of the invention, wherein an effective amount is the amount suitable for obtaining the required antimicrobial effect in the chosen application. In one aspect, the use of the composition of the invention in an animal inhibits the growth of microbial cells, e.g. the antimicrobial composition is a bacteriostatic.

In another embodiment, use of a composition comprising a lactose oxidase and a vanadium haloperoxidase to control the growth of microorganisms in an animal comprises feeding the animal with an antimicrobial composition that kills the growth of microbial cells, e.g. the antimicrobial composition is bactericidal. In a preferred embodiment, the use of the composition of the invention in an animal comprises feeding the animal with an antimicrobial composition that kills at least 90%, such as at least 99%, at least 99.5%, at least 99.7%, at least 99.9%, at least 99.95%, at least 99.97%, at least 99.99% of the number of bacterium, wherein the bacterium is from the genus *Salmonella, Escherichia, Campylobacter, Listeria* and/or *Clostridium*, preferably from *Escherichia*, more preferably from *E. Coli*, even more preferably from *E. Coli* K12.

In a further embodiment, the lactose oxidase is the polypeptide of SEQ ID NO: 1 and the vanadium haloperoxidase is the polypeptide of SEQ ID NO: 2. In a further embodiment, the lactose oxidase is the polypeptide of SEQ ID NO: 1 and the vanadium haloperoxidase is the polypeptide of SEQ ID NO: 3. In a further embodiment, the lactose oxidase is the polypeptide of SEQ ID NO: 1 and the vanadium haloperoxidase is the polypeptide of SEQ ID NO: 5. In a further embodiment, the lactose oxidase is the polypeptide of SEQ ID NO: 1 and the vanadium haloperoxidase is the polypeptide of SEQ ID NO: 6. In a further embodiment, the lactose oxidase is the polypeptide of SEQ ID NO: 1 and the vanadium haloperoxidase is the polypeptide of SEQ ID NO: 7. In a further embodiment, the lactose oxidase is the polypeptide of SEQ ID NO: 1 and the vanadium haloperoxidase is the polypeptide of SEQ ID NO: 8.

Compositions Comprising Lactose Oxidases and Vanadium Haloperoxidases

A further aspect of the invention is a composition comprising one or more lactose oxidases and one or more vanadium haloperoxidases. In an embodiment, the composition further comprises one or more additional compounds selected from the list consisting of forage, concentrates, vitamins, minerals, amino acids, enzymes and other feed ingredients, as defined herein. In a further embodiment, the composition is used to control the growth of microorganisms in an animal. In an embodiment, the composition controls the growth of microorganisms in an animal that is not human. In an embodiment, the composition contains no Lactoferrin. In an embodiment, the lactose oxidase and vanadium haloperoxidase are gastric stable.

In another aspect of the invention, the composition is an animal feed additive or premix, comprising one or more lactose oxidases, one or more vanadium haloperoxidases and one or more components selected from the list consisting of vitamins, minerals, amino acids, enzymes and other feed ingredients. In an embodiment, the animal feed additive comprises one or more lactose oxidases, one or more vanadium haloperoxidases and one or more vitamins. In an embodiment, the animal feed additive comprises one or more lactose oxidases, one or more vanadium haloperoxidases and one or more minerals. In an embodiment, the animal feed additive comprises one or more lactose oxidases, one or more vanadium haloperoxidases and one or more amino acids. In an embodiment, the animal feed additive comprises one or more lactose oxidases, one or more vanadium haloperoxidases and one or more enzymes.

In another aspect of the invention, the composition is an animal feed, comprising one or more lactose oxidases, one or more vanadium haloperoxidases, forage and optionally concentrate and/or a premix. In another aspect of the invention, the composition is an animal feed, comprising one or more lactose oxidases, one or more vanadium haloperoxidases, concentrates and optionally forage and/or a premix. The premix comprises one or more components selected from the list consisting of vitamins, minerals, amino acids, enzymes and other feed ingredients.

A preferred embodiment is an animal feed comprising one or more lactose oxidases, one or more vanadium haloperoxidases, one or more polypeptides selected from the list amylases; phytases; xylanases; galactanases; alpha-galactosidases; proteases, phospholipases, beta-glucanases, or any mixture thereof, together with one or more vitamins and/or one or more minerals. In an embodiment, the composition does not contain Lactoferrin.

In another embodiment, the composition comprising a lactose oxidase and a vanadium haloperoxidase kills the growth of microbial cells, e.g. the antimicrobial composition is bactericidal. In a preferred embodiment, the composition of the invention kills at least 90%, such as at least 99%, at least 99.5%, at least 99.7%, at least 99.9%, at least 99.95%, at least 99.97%, at least 99.99% of the number of bacterium, wherein the bacterium is from the genus *Salmonella, Escherichia, Campylobacter, Listeria* and/or *Clostridium*, preferably from *Escherichia*, more preferably from *E. Coli*, even more preferably from *E. Coli* K12.

In a further embodiment, the lactose oxidase is the polypeptide of SEQ ID NO: 1 and the vanadium haloperoxidase is the polypeptide of SEQ ID NO: 2. In a further embodiment, the lactose oxidase is the polypeptide of SEQ ID NO: 1 and the vanadium haloperoxidase is the polypeptide of SEQ ID NO: 3. In a further embodiment, the lactose oxidase is the polypeptide of SEQ ID NO: 1 and the vanadium haloperoxidase is the polypeptide of SEQ ID NO: 5. In a further embodiment, the lactose oxidase is the polypeptide of SEQ ID NO: 1 and the vanadium haloperoxidase is the polypeptide of SEQ ID NO: 6. In a further embodiment, the lactose oxidase is the polypeptide of SEQ ID NO: 1 and the vanadium haloperoxidase is the polypeptide of SEQ ID NO: 7. In a further embodiment, the lactose oxidase is the polypeptide of SEQ ID NO: 1 and the vanadium haloperoxidase is the polypeptide of SEQ ID NO: 8.

Methods for the Treatment of Animal Feed

Another aspect of the invention is a method for the treatment of animal feed comprising mixing the animal feed with one or more lactose oxidases and one or more vanadium haloperoxidases. The antimicrobial additive, which comprises lactose oxidases and vanadium haloperoxidases, is preferably added to the mash feed which is then conditioned, pelleted and cooled. Said animal feed then comprises one or more lactose oxidases and one or more vanadium haloperoxidases that can act as an antimicrobial agent whilst the feed is stored. Thus when the feed is eaten by the animal, the risk that the animal will eat contaminated feed is thereby reduced. The animal feed can further act as an antimicrobial agent in the gut of the animal as hereby described in other aspects of the invention.

In an embodiment, the lactose oxidase and vanadium haloperoxidase are gasatric stable. The composition may also comprise one or more sources of halide, hydrogen peroxide and/or one or more sources of hydrogen peroxide, such as cellobiose, lactose, maltose, and/or raffinose. In another aspect, the antimicrobial composition of the invention further comprises forage, concentrates, vitamins, minerals, amino acids, enzymes and/or other feed ingredients, as defined herein.

The method for the treatment of animal feed may be carried out with an effective amount of the antimicrobial additive of the invention, wherein an effective amount is the amount suitable for obtaining the required antimicrobial effect in the chosen application. In one aspect, method for the treatment of animal feed comprises mixing the animal feed with the antimicrobial additive of the invention that inhibits the growth of microbial cells in the animal feed, e.g. the antimicrobial additive is a bacteriostatic.

In another embodiment, the method for the treatment of animal feed comprises mixing the animal feed with an additive comprising one or more lactose oxidases and one or more vanadium haloperoxidases such that the composition kills the growth of microbial cells, e.g. the additive is bactericidal. In a preferred embodiment, the method for the treatment of animal feed comprises mixing the animal feed with an antimicrobial additive of the invention that kills at least 90%, such as at least 99%, at least 99.5%, at least 99.7%, at least 99.9%, at least 99.95%, at least 99.97%, at least 99.99% of the number of bacterium in the animal feed, wherein the bacterium is from the genus *Salmonella, Escherichia, Campylobacter, Listeria* and/or *Clostridium*, preferably from *Escherichia*, more preferably from *E. Coli*, even more preferably from *E. Coli* K12.

In a further embodiment, the lactose oxidase is the polypeptide of SEQ ID NO: 1 and the vanadium haloperoxidase is the polypeptide of SEQ ID NO: 2. In a further embodiment, the lactose oxidase is the polypeptide of SEQ ID NO: 1 and the vanadium haloperoxidase is the polypeptide of SEQ ID NO: 3. In a further embodiment, the lactose oxidase is the polypeptide of SEQ ID NO: 1 and the vanadium haloperoxidase is the polypeptide of SEQ ID NO: 5. In a further embodiment, the lactose oxidase is the polypeptide of SEQ ID NO: 1 and the vanadium haloperoxidase is the polypeptide of SEQ ID NO: 6. In a further embodiment, the lactose oxidase is the polypeptide of SEQ ID NO: 1 and the vanadium haloperoxidase is the polypeptide of SEQ ID NO: 7. In a further embodiment, the lactose oxidase is the polypeptide of SEQ ID NO: 1 and the vanadium haloperoxidase is the polypeptide of SEQ ID NO: 8.

Animal Feed

In the context of this invention, an animal feed or feed additive is an enzyme preparation comprising one or more enzyme(s) and suitable carriers and/or excipients, and which enzyme preparation is provided in a form that is suitable for being added to animal feed. The animal feed additive of the invention may be prepared in accordance with methods known in the art and may be in the form of a dry or a liquid preparation. The enzyme to be included in the preparation may optionally be stabilized in accordance with methods known in the art.

In one aspect, the animal feed, comprises forage and may further comprise concentrates as well as vitamins, minerals, enzymes, amino acids and/or other feed ingredients (incorporated from e.g. a premix). Such an animal feed is generally suitable for ruminants, such as sheep, goats, and cattle etc. In another aspect, the animal feed, comprises concentrates and may further comprise vitamins, minerals, enzymes, amino acids and/or other feed ingredients (incorporated from e.g. a premix) and optionally forage. Such an animal feed is generally suitable for non-ruminants, such as pigs and poultry etc.

Thus another aspect of the invention is a method for preparing an animal feed composition, comprising mixing a lactose oxidase, a vanadium haloperoxidase, and one or more animal feed ingredients selected from the list consisting of forage, concentrates, vitamins, minerals, amino acids, and animal feed enzymes.

Forage

Forage as defined herein also includes roughage. Forage is fresh plant material such as hay and silage from forage plants, grass and other forage plants, grass and other forage plants, seaweed, sprouted grains and legumes, or any combination thereof. Examples of forage plants are Alfalfa (lucerne), birdsfoot trefoil, brassica (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothygrass), corn (maize), millet, barley, oats, rye, sorghum, soybeans and wheat and vegetables such as beets. Crops suitable for ensilage are the ordinary grasses, clovers, alfalfa, vetches, oats, rye and maize. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Roughage is generally dry plant material with high levels of fiber, such as fiber, bran, husks from seeds and grains and crop residues (such as stover, copra, straw, chaff, sugar beet waste).

Concentrates

Concentrates are feed with high protein and energy concentrations, such as fish meal, molasses, oligosaccharides, sorghum, seeds and grains (either whole or prepared by crushing, milling, etc from e.g. corn, oats, rye, barley, wheat), oilseed press cake (e.g. from cottonseed, safflower, sunflower, soybean, oilseed rape/canola, peanut or groundnut), palm kernel cake, yeast derived material and distillers grains (such as wet distillers grains (WDS) and dried distillers grains with solubles (DDGS)).

Premix or Feed Additive

In an embodiment, the animal feed may include a premix (also called feed additive), comprising e.g. vitamins, minerals, enzymes, preservatives, antibiotics, other feed ingredients or any combination thereof which is mixed into the animal feed.

Vitamins and Minerals

The animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed. Non-limiting examples of fat-soluble vitamins include vitamin A, vitamin D3, vitamin E, and vitamin K, e.g., vitamin K3. Non-limiting examples of water-soluble vitamins include vitamin B12, biotin and choline, vitamin B1, vitamin B2, vitamin B6, niacin, folic acid and panthothenate, e.g., Ca-D-panthothenate. Non-limiting examples of trace minerals include boron, cobalt, chloride, chromium, copper, fluoride, iodine, iron, manganese, molybdenum, selenium and zinc. Non-limiting examples of macro minerals include calcium, magnesium, potassium and sodium.

Enzymes

In another embodiment, the animal feed described herein optionally includes one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy(ModO) internet site (Coutinho, P. M. & Henrissat, B. (1999) Carbohydrate-Active Enzymes server at URL: http://afmb.cnrs-mrs.fr/~cazy/CAZY/index.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation"., K. Ohmiya, K. Hayashi, K. Sakka, Y. Kobayashi, S. Karita and T. Kimura eds., Uni Publishers Co., Tokyo, pp. 15-23).

Thus the animal feed may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and beta-glucanase (EC 3.2.1.4 or EC 3.2.1.6), or any mixture thereof.

In a particular embodiment, the animal feed comprises a phytase (EC 3.1.3.8 or 3.1.3.26). Examples of commercially available phytases include Bio-Feed™ Phytase (Novozymes), Ronozyme® P and HiPhos™ (DSM Nutritional Products), Natuphos™ (BASF), Finase® and Quantum® Blue (AB Enzymes), the Phyzyme® XP (Verenium/DuPont) and Axtra® PHY (DuPont). Other preferred phytases include those described in e.g. WO 98/28408, WO 00/43503, and WO 03/066847.

In a particular embodiment, the animal feed comprises a xylanase (EC 3.2.1.8). Examples of commercially available xylanases include Ronozyme® WX and G2 (DSM Nutritional Products), Econase® XT and Barley (AB Vista), Xylathin® (Verenium) and Axtra® XB (Xylanase/beta-glucanase, DuPont)

In a particular embodiment, the animal feed comprises a protease (EC 3.4). Examples of commercially available proteases include Ronozyme® ProAct (DSM Nutritional Products).

Amino Acids

The animal feed may further comprise one or more amino acids. Examples of amino acids which are used in animal feed are lysine, alanine, beta-alanine, threonine, methionine and tryptophan.

Other Feed Ingredients

The animal feed may further comprise colouring agents, stabilisers, growth improving additives and aroma compounds/flavorings, polyunsaturated fatty acids (PUFAs); reactive oxygen generating species, anti-microbial peptides and anti-fungal polypeptides.

Examples of colouring agents are carotenoids such as beta-carotene, astaxanthin, and lutein.

Examples of aroma compounds/flavorings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Manufacturing

Animal diets can e.g. be manufactured as mash feed (non-pelleted) or pelleted feed. Typically, the milled feedstuffs are mixed and sufficient amounts of essential vitamins and minerals are added according to the specifications for the species in question. The bacteria cultures and optionally enzymes can be added as solid or liquid formulations. For example, for mash feed a solid or liquid culture formulation may be added before or during the ingredient mixing step. For pelleted feed the (liquid or solid) culture preparation may also be added before or during the feed ingredient step. Typically a liquid culture preparation comprises the culture of the invention optionally with a polyol, such as glycerol, ethylene glycol or propylene glycol, and is added after the pelleting step, such as by spraying the liquid formulation onto the pellets. The enzymes may also be incorporated in a feed additive or premix.

The enzymes may be added to the feed mix as a granule, which is optionally pelleted or extruded. The granule typically comprises a core particle and one or more coatings, which typically are salt and/or wax coatings. The core particle can either be a homogeneous blend of an active compound optionally together with salts (e.g. organic or inorganic zinc or calcium salt) or an inert particle with an active compound applied onto it. The active compound is the culture of the invention optionally combined with the enzymes of the invention. The inert particle may be water soluble or water insoluble, e.g. starch, a sugar (such as sucrose or lactose), or a salt (such as NaCl, $Na_2SO_4$). The salt coating is typically at least 1 μm thick and can either be one particular salt or a mixture of salts, such as $Na_2SO_4$, $K_2SO_4$, $MgSO_4$ and/or sodium citrate. Other examples are those described in e.g. WO 2008/017659, WO 2006/034710, WO 1997/05245, WO 1998/54980, WO 1998/55599, WO 2000/70034 or polymer coating such as described in WO 2001/00042.

Alternatively, the enzymes of the invention can be prepared by freezing a mixture of liquid culture solution with a bulking agent such as ground soybean meal, and then lyophilizing the mixture.

Lactose Oxidase

Oxidoreductases are enzymes that catalyze the transfer of electrons from one molecule to another. Dehydrogenases and oxidases belong to the enzyme class of oxidoreductases. Generally, dehydrogenases need the presence of a cofactor, e.g. NAD/NADP or a flavin coenzyme such as FAD or FMN, but this may also be the case for oxidases. Unless anything else is suggested, the enzymes described below and throughout the description are isolated enzymes with co-factor, if required.

One category of oxidoreductases are carbohydrate oxidases that catalyze an oxidation/reduction reaction involving molecular oxygen ($O_2$) as the electron acceptor and a sugar. In these reactions, oxygen is reduced to water ($H_2O$) or hydrogen peroxide ($H_2O_2$). The net reaction scheme may be described as:

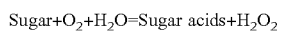

$$Sugar+O_2+H_2O=Sugar\ acids+H_2O_2$$

A preferred class of carbohydrate oxidase is a lactose oxidase. According to this invention, lactose oxidases are enzymes that have at least one of cellobiose oxidase activity (also called cellobiose dehydrogenase, EC 1.1.99.18, formally EC 1.1.3.25), lactose oxidase activity or maltose oxidase activity. Thus they are capable of oxidising cellobiose, lactose, maltose, raffinose, glucose, lactulose and/or xylose, preferably cellobiose, lactose, maltose, and/or raffinose.

Enzymes having cellobiose oxidase activity, e.g. cellobiose oxidases, are capable of oxidizing several saccharides including cellobiose, soluble cellooligosaccharides, lactose, xylobiose and maltose. Enzymes belonging to the class of cellobiose oxidases are also preferred enzymes in the present invention. Cellobiose oxidase is an extracellular enzyme produced by various wood-degrading fungi, such as the white-rot fungus *Phanerochaete chrysosporium*, brown-rot fungus Coniophora puteana and soft-rot fungi such as *Monilia* sp., *chaetomium, cellulolyticum, Myceliophthora (Sporotrichum) thermophila, Sclerotium rolfsii* and *Humicola insolens* (Schou et al., 1998, Biochemical Journal 330: 565-571).

Lactose oxidases have significantly broader substrate specificity over other carbohydrate oxidases, such as glucose oxidases, which is advantageous since there is a higher chance of finding a relevant substrate in the animal feed for the enzyme to act upon. This can clearly be seen from table 1, where the specificity of the lactose oxidase from *Microdochium nivale* deposited under CBS 100236 (SEQ ID NO: 1) is compared to a glucose oxidase from *Aspergillus niger* (UNIPROT: P13006)

TABLE 1

| Relative activities of a lactose oxidase and glucose oxidase | | |
|---|---|---|
| Substrate | % Activity for lactose oxidase from *Microdochium nivale* | % Activity for glucose oxidase from *Aspergillus niger* |
| D-(+)-Cellobiose | 88 | 0 |
| D-Lactose | 100 | 0 |
| D-Maltose | 99 | 0 |
| D-Raffinose | 53 | 0 |
| D-(+)-Glucose | 43 | 100 |
| Lactulose | 31 | 0 |
| D-(+)-Xylose | 22 | 0 |
| 2-Deoxy-D-glucose | 4 | 16 |

Activity is set to the optimal activity for that enzyme at pH 7 (lactose for lactose oxidase, glucose for glucose oxidase) as determined using the method described in example 12 of US2003/0180416. All other relative activities tested are under 10% for lactose oxidase and 1% for glucose oxidase and are excluded from the table.

In another preferred embodiment, the lactose oxidase is preferably obtained from a fungus belonging to the genus

*Microdochium*, more preferably *Microdochium nivale* and even more preferably *Microdochium nivale* deposited under CBS 100236. The lactose oxidase isolated from CBS 100236 is described in detail in WO 99/31990 (SEQ ID NO: 2 of WO 99/31990; also shown as SEQ ID NO: 1 of the present application). In a preferred embodiment, the amino acid sequence of the lactose oxidase has at least 70% sequence identity to the polypeptide of SEQ ID NO: 1. In a more preferred embodiment, the amino acid sequence of the lactose oxidase has at least 80% sequence identity to the polypeptide of SEQ ID NO: 1. In an even more preferred embodiment, the amino acid sequence of the lactose oxidase has at least 90% sequence identity to the polypeptide of SEQ ID NO: 1. In an even more preferred embodiment, the amino acid sequence of the lactose oxidase has at least 95%, such as at least 96%, at least 97%, at least 98%, or at least 99% sequence identity to the polypeptide of SEQ ID NO: 1. In a further embodiment, the lactose oxidase is the polypeptide of SEQ ID NO: 1.

In another aspect, the lactose oxidase differs by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 1.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for haloperoxidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

The concentration of the lactose oxidase is typically in the range of 0.01-10000 ppm enzyme protein per kg feed, preferably 0.1-5000 ppm, more preferably 0.5-2500 ppm, even more preferably 2-1000 ppm, and most preferably 5-500 ppm enzyme protein per kg feed, which corresponds to 5-500 mg per kg feed.

Vanadium Haloperoxidase

Haloperoxidases form a class of enzymes which are able to oxidize halides (X=Cl—, Br—, or I—) in the presence of hydrogen peroxide to the corresponding hypohalous acid (HOX) according to:

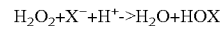

$$H_2O_2 + X^- + H^+ \rightarrow H_2O + HOX$$

If a convenient nucleophilic acceptor is present, a reaction will occur with HOX whereby a diversity of halogenated reaction products may be formed.

Haloperoxidases form a class of enzymes that are capable of oxidizing halides ($Cl^-$, $Br^-$, $I^-$) and thiocyanate ($SCN^-$) in the presence of hydrogen peroxide or a hydrogen peroxide generating system to the corresponding hypohalous acids or hypohalites; or in the case of thiocyanate, to hypothiocyanous acid or hypothiocyanite.

Haloperoxidases are classified according to their specificity for halide ions. Chloroperoxidases (E.C. 1.11.1.10) catalyse formation of hypochlorite from chloride ions, hypobromite from bromide ions and hypoiodite from iodide ions; and bromoperoxidases (E.C. 1.11.1.18) catalyze formation of hypobromite from bromide ions and hypoiodite from iodide ions. Hypoiodite, however, with iodide dispropor-tionates to form elemental iodine and thus iodine is the observed product. The hypohalite compounds may subsequently react with other compounds forming halogenated compounds.

Haloperoxidases have been isolated from various organisms: mammals, marine animals, plants, algae, lichen, fungi and bacteria. It is generally accepted that haloperoxidases are the enzymes responsible for the formation of halogenated compounds in nature, although other enzymes may be involved.

The haloperoxidase of the invention is a vanadium haloperoxidase, i.e. a vanadate-containing haloperoxidase. Vanadium haloperoxidases may be a vanadium chloroperoxidase or a vanadium bromoperoxidase, preferably a vanadium chloroperoxidase, and are different from other haloperoxidases in that the prosthetic group in theses enzymes have structural features similar to vanadate (vanadium V), whereas the other haloperoxidases are hemeperoxidases. Vanadium haloperoxidases have been isolated from various organisms such as mammals, marine animals, plants, algae, lichen, fungi and bacteria (see Johannes, W. P. M. et al, 1993, *Biochimica et Biophysica Acta—Protein Structure and Molecular Enzymology* 1161: 249-256).

In a preferred embodiment, the vanadium haloperoxidase is derivable from a species of *Curvularia*. In one preferred embodiment, the haloperoxidase is derivable from *Curvularia verruculosa*, such as *C. verruculosa* CBS 147.63 or *C. verruculosa* CBS 444.70, as described in WO 97/04102 (see SEQ ID NO: 2 in WO 97/04102; also shown as SEQ ID NO: 2 of the present application). In a preferred embodiment, the amino acid sequence of the vanadium haloperoxidase has at least 70% sequence identity to the polypeptide of SEQ ID NO: 2. In a more preferred embodiment, the amino acid sequence of the vanadium haloperoxidase has at least 75% sequence identity to the polypeptide of SEQ ID NO: 2. In a more preferred embodiment, the amino acid sequence of the vanadium haloperoxidase has at least 80% sequence identity to the polypeptide of SEQ ID NO: 2. In a more preferred embodiment, the amino acid sequence of the vanadium haloperoxidase has at least 85% sequence identity to the polypeptide of SEQ ID NO: 2. In an even more preferred embodiment, the amino acid sequence of the vanadium haloperoxidase has at least 90% sequence identity to the polypeptide of SEQ ID NO: 2. In an even more preferred embodiment, the amino acid sequence of the vanadium haloperoxidase has at least 95%, such as at least 96%, at least 97%, at least 98%, or at least 99% sequence identity to the polypeptide of SEQ ID NO: 2. In a further embodiment, the vanadium haloperoxidase is the polypeptide of SEQ ID NO: 2.

In another aspect, the vanadium haloperoxidase differs by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 2.

In another preferred embodiment, the vanadium haloperoxidase is derivable from *Curvularia inaequalis*, such as *C. inaequalis* CBS 102.42, as described in WO 95/27046 (a vanadium haloperoxidase encoded by the DNA sequence of WO 95/27046, FIG. 2; also shown as SEQ ID NO: 3 of the present application). In a preferred embodiment, the amino acid sequence of the vanadium haloperoxidase has at least 70% sequence identity to the polypeptide of SEQ ID NO: 3. In a more preferred embodiment, the amino acid sequence of the vanadium haloperoxidase has at least 75% sequence identity to the polypeptide of SEQ ID NO: 3. In a more preferred embodiment, the amino acid sequence of the vanadium haloperoxidase has at least 80% sequence identity to the polypeptide of SEQ ID NO: 3. In a more preferred embodiment, the amino acid sequence of the vanadium haloperoxidase has at least 85% sequence identity to the polypeptide of SEQ ID NO: 3. In an even more preferred embodiment, the amino acid sequence of the vanadium haloperoxidase has at least 90% sequence identity to the polypeptide of SEQ ID NO: 3. In an even more preferred embodiment, the amino acid sequence of the vanadium haloperoxidase has at least 95%, such as at least 96%, at least 97%, at least 98%, or at least 99% sequence identity to the polypeptide of SEQ ID NO: 3. In a further embodiment, the vanadium haloperoxidase is the polypeptide of SEQ ID NO: 3.

In another aspect, the vanadium haloperoxidase differs by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 3.

In another preferred embodiment, the vanadium haloperoxidase is derivable from *Drechslera hartlebii* as described in 01/79459 (SEQ ID NO: 5 of the present application). In a preferred embodiment, the amino acid sequence of the vanadium haloperoxidase has at least 70% sequence identity to the polypeptide of SEQ ID NO: 5. In a more preferred embodiment, the amino acid sequence of the vanadium haloperoxidase has at least 75% sequence identity to the polypeptide of SEQ ID NO: 5. In a more preferred embodiment, the amino acid sequence of the vanadium haloperoxidase has at least 80% sequence identity to the polypeptide of SEQ ID NO: 5. In a more preferred embodiment, the amino acid sequence of the vanadium haloperoxidase has at least 85% sequence identity to the polypeptide of SEQ ID NO: 5. In an even more preferred embodiment, the amino acid sequence of the vanadium haloperoxidase has at least 90% sequence identity to the polypeptide of SEQ ID NO: 5. In an even more preferred embodiment, the amino acid sequence of the vanadium haloperoxidase has at least 95%, such as at least 96%, at least 97%, at least 98%, or at least 99% sequence identity to the polypeptide of SEQ ID NO: 5. In a further embodiment, the vanadium haloperoxidase is the polypeptide of SEQ ID NO: 5.

In another aspect, the vanadium haloperoxidase differs by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 5.

In another preferred embodiment, the vanadium haloperoxidase is derivable from *Dendryphiella salina*, as described in WO 01/79458 (SEQ ID NO: 6 of the present application). In a preferred embodiment, the amino acid sequence of the vanadium haloperoxidase has at least 70% sequence identity to the polypeptide of SEQ ID NO: 6. In a more preferred embodiment, the amino acid sequence of the vanadium haloperoxidase has at least 75% sequence identity to the polypeptide of SEQ ID NO: 6. In a more preferred embodiment, the amino acid sequence of the vanadium haloperoxidase has at least 80% sequence identity to the polypeptide of SEQ ID NO: 6. In a more preferred embodiment, the amino acid sequence of the vanadium haloperoxidase has at least 85% sequence identity to the polypeptide of SEQ ID NO: 6. In an even more preferred embodiment, the amino acid sequence of the vanadium haloperoxidase has at least 90% sequence identity to the polypeptide of SEQ ID NO: 6. In an even more preferred embodiment, the amino acid sequence of the vanadium haloperoxidase has at least 95%, such as at least 96%, at least 97%, at least 98%, or at least 99% sequence identity to the polypeptide of SEQ ID NO: 6. In a further embodiment, the vanadium haloperoxidase is the polypeptide of SEQ ID NO: 6.

In another aspect, the vanadium haloperoxidase differs by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 6.

In another preferred embodiment, the vanadium haloperoxidase is derivable from *Phaeotrichoconis crotalarie*, as described in WO 01/79461 (SEQ ID NO: 7 of the present application). In a preferred embodiment, the amino acid sequence of the vanadium haloperoxidase has at least 70% sequence identity to the polypeptide of SEQ ID NO: 7. In a more preferred embodiment, the amino acid sequence of the vanadium haloperoxidase has at least 75% sequence identity to the polypeptide of SEQ ID NO: 7. In a more preferred embodiment, the amino acid sequence of the vanadium haloperoxidase has at least 80% sequence identity to the polypeptide of SEQ ID NO: 7. In a more preferred embodiment, the amino acid sequence of the vanadium haloperoxidase has at least 85% sequence identity to the polypeptide of SEQ ID NO: 7. In an even more preferred embodiment, the amino acid sequence of the vanadium haloperoxidase has at least 90% sequence identity to the polypeptide of SEQ ID NO: 7. In an even more preferred embodiment, the amino acid sequence of the vanadium haloperoxidase has at least 95%, such as at least 96%, at least 97%, at least 98%, or at least 99% sequence identity to the polypeptide of SEQ ID NO: 7. In a further embodiment, the vanadium haloperoxidase is the polypeptide of SEQ ID NO: 7.

In another aspect, the vanadium haloperoxidase differs by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 7.

In another preferred embodiment, the vanadium haloperoxidase is derivable from *Geniculosporium* sp., as described in WO 01/79460 (SEQ ID NO: 8 of the present application). In a preferred embodiment, the amino acid sequence of the vanadium haloperoxidase has at least 70% sequence identity to the polypeptide of SEQ ID NO: 8. In a more preferred embodiment, the amino acid sequence of the vanadium haloperoxidase has at least 75% sequence identity to the polypeptide of SEQ ID NO: 8. In a more preferred embodiment, the amino acid sequence of the vanadium haloperoxidase has at least 80% sequence identity to the polypeptide of SEQ ID NO: 8. In a more preferred embodiment, the amino acid sequence of the vanadium haloperoxidase has at least 85% sequence identity to the polypeptide of SEQ ID NO: 8. In an even more preferred embodiment, the amino acid sequence of the vanadium haloperoxidase has at least 90% sequence identity to the polypeptide of SEQ ID NO: 8. In an even more preferred embodiment, the amino acid sequence of the vanadium haloperoxidase has at least 95%, such as at least 96%, at least 97%, at least 98%, or at least 99% sequence identity to the polypeptide of SEQ ID NO: 8. In a further embodiment, the vanadium haloperoxidase is the polypeptide of SEQ ID NO: 8.

In another aspect, the vanadium haloperoxidase differs by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 8.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids and active sites in a polypeptide can be identified as previously described. Single or multiple amino acid substitutions, deletions, and/or insertions can be made and tested using known methods as described above. The sequence identity of SEQ ID NO: 2, 3, 5, 6, 7 and 8, when calculated as defined herein, shows that the sequence are well conserved such that all sequences are at least 75% identical to each other.

The concentration of the vanadium haloperoxidase is typically in the range of 0.01-10000 ppm enzyme protein, preferably 0.1-2500 ppm, more preferably 0.5-1000 ppm, even more preferably 1-400 ppm, and most preferably 2-200 ppm enzyme protein, which corresponds to 2-200 mg per kg feed.

Hydrogen Peroxide Sources

The hydrogen peroxide required by the vanadium haloperoxidase may be provided as an aqueous solution of hydrogen peroxide or a hydrogen peroxide precursor for in situ production of hydrogen peroxide. Any solid entity which liberates upon dissolution a peroxide, which is useable by the vanadium haloperoxidase, can serve as a source of hydrogen peroxide. Compounds which yield hydrogen peroxide upon dissolution in water or an appropriate aqueous based medium include but are not limited to metal peroxides, percarbonates, persulphates, perphosphates, peroxyacids, alkyperoxides, acylperoxides, peroxyesters, urea peroxide, perborates and peroxycarboxylic acids or salts thereof.

Another source of hydrogen peroxide is a hydrogen peroxide generating enzyme system, such as a lactose oxidase together with a substrate for the oxidase. Examples of substrates that lactose oxidase works with are cellobiose, lactose, maltose, raffinose, glucose, lactulose and/or xylose, preferably cellobiose, lactose, maltose, and/or raffinose.

It may be advantageous to use enzymatically generated hydrogen peroxide, since this source results in a relatively low concentration of hydrogen peroxide under the biologically relevant conditions. Low concentrations of hydrogen peroxide result in an increase in the rate of haloperoxidase-catalysed reaction.

Halide Sources

Generally, halides needed for reaction with the vanadium haloperoxidase are available in sufficient amounts in feed compositions (e.g., as the chloride salt of a compound in the premix). However, if necessary, a source of halide ions may be added to the composition such as by adding a halide salt. The halide salt(s) may be chloride salt(s) such as sodium chloride (NaCl), potassium chloride (KCl), or ammonium chloride ($NH_4Cl$), bromide salt(s) such as sodium bromide (NaBr), potassium bromide (KBr), or ammonium bromide ($NH_4Br$), iodide salt(s) such as sodium iodide (NaI), potassium iodide (KI), or ammonium iodide (NH₄I), thiocyanate salt(s) such as sodium thiocyanate (NaSCN), potassium thiocyanate (KSCN), or ammonium thiocyanate (NH₄SCN), or any mixtures thereof.

The concentration of chloride, bromide, iodide, and/or thiocyanate ions are collectively or individually in the range of 0.1-10000 ppm chloride, bromide, iodide, and/or thiocyanate per kg feed, preferably in the range of from 1-5000 ppm chloride, bromide, iodide, and/or thiocyanate per kg feed, more preferably in the range 10-2000 ppm chloride, bromide, iodide, and/or thiocyanate per kg feed.

The present invention is further described by the following examples that should not be construed as limiting the scope of the invention.

EXAMPLES

Example 1

Antimicrobial Activity of a Composition Comprising a Lactose Oxidase and a Vanadium Haloperoxidase The lactose oxidase (COX) used was isolated from *Microdochium nivale* CBS 100236 and described in detail in WO 99/31990 (SEQ ID NO: 2 of WO 99/31990; also shown as SEQ ID NO: 1 of the present application) at a concentration of 15 mg enzyme protein/mL.

The vanadium haloperoxidase (HAP) used was isolated from *Curvularia verruculosa* CBS 147.63, as described in WO 97/04102 (see SEQ ID NO: 2 in WO 97/04102; also shown as SEQ ID NO: 2 of the present application) at a concentration of 33 mg enzyme protein/mL.

The amino acid oxidase (AAO) is a L-lysine oxidase and was isolated from *Trichoderma harzianum* CBS 223.93, as described in U.S. Pat. No. 6,248,575 (also shown as SEQ ID NO: 4 of the present application).

The antibacterial activity of lactose oxidase (COX), vanadium haloperoxidase (HAP) and amino acid oxidase (AAO) against *Escherichia coli* was studied. *E. coli* K12 was inoculated in 10 mL luria broth (LB) and left overnight at 37° C. Tris buffer was diluted to 10× in MQ water. The diluted tris buffer was adjusted to pH 6.3 using 1M hydrochloric acid. Chicken feed (30:70 weight ratio blend of soya bean meal and maize meal, 2 g) was weighed and transferred to each of two 50 mL tubes containing either 10 mL of 0.1 M acetate buffer at pH 3 or 10 mL of 0.1 M tris buffer at pH 6.3. 100 μL of *E. coli* from the overnight culture was transferred to each of the two feed suspensions. 5×1 mL aliquots of each feed suspension were made. Enzymes lactose oxidase, vanadium haloperoxidase and amino acid oxidase were added to the aliquots as shown in Table 2 compared to two controls without enzymes with pH 3 and 6 respectively. The enzymatic treatment of the feed was carried out at 40° C. for one hour at 300 rpm. After treatment a dilution range of $10^{-4}$ was carried out in a sterile 0.9% sodium chloride solution (100 μL to 900 μL of sodium chloride in water). The dilutions were dot-spotted on LB agar plates (10 μL per spot) and incubated overnight at 37° C. The colony forming units (CFU) were counted in spots with lower than 30 colonies. The results are given in FIG. 1 and table 3.

TABLE 2

Amount of lactose oxidase, vanadium haloperoxidase and amino acid oxidase used

| Experiment | pH | Lactose Oxidase (μL) | Amino Acid Oxidase (μL) | Vanadium Haloperoxidase (μL) |
|---|---|---|---|---|
| 1 | 3 | 10 | — | 1 |
| 2 | 3 | 10 | — | — |
| 3 | 3 | — | — | 1 |
| 4 | 6 | — | 10 | 1 |
| 5 | 6 | — | 10 | — |
| 6 | 6 | — | — | 1 |
| 7 | 3 | — | 10 | 1 |
| 8 | 6 | 10 | — | 1 |
| Control 1 | 3 | — | — | — |
| Control 2 | 6 | — | — | — |

TABLE 3

Surviving *E. coli* K12 in contaminated feed when treated with a lactose oxidase, vanadium haloperoxidase and/or amino acid oxidase

| Experiment | CFU | Dilution Factor | Surviving *E. coli* K12 (CFU/mL) |
|---|---|---|---|
| 1 | 0 | 100 | <100 |
| 2 | 6 | $10^6$ | 6.000.000 |
| 3 | 30 | $10^6$ | 30.000.000 |
| 4 | ~100 | $10^6$ | 100.000.000 |
| 5 | ~80 | $10^6$ | 80.000.000 |
| 6 | ~100 | $10^6$ | 100.000.000 |
| 7 | 23 | $10^6$ | 23.000.000 |
| 8 | 0 | 100 | <100 |
| pH 3 | 39 | $10^6$ | 39.000.000 |
| pH 6 | ~50 | $10^6$ | 50.000.000 |

As can be seen in table 3 and FIG. 1, treatment of feed contaminated with *E. coli* K12 with a lactose oxidase and a vanadium haloperoxidase was able to efficiently kill over 99.99% of the *E. coli* K12 cells in the contaminated feed broth at both pH 3 and pH 6. However, neither a lactose oxidase, a vanadium haloperoxidase or amino acid oxidase and vanadium haloperoxidase were able to reduce the CFU of *E. coli* K12 cells by more than one log unit.

Example 2

Residual Antimicrobial Activity of a Composition Comprising a Lactose Oxidase and a Vanadium Haloperoxidase Following Incubation in Simulated Gastric Juice The lactose oxidase (COX) used was isolated from *Microdochium nivale* CBS 100236 and described in detail in WO 99/31990 (SEQ ID NO: 2 of WO 99/31990; also shown as SEQ ID NO: 1 of the present application) at a concentration of 15 mg enzyme protein/mL.

The vanadium haloperoxidase (HAP) used was isolated from *Curvularia verruculosa* CBS 147.63, as described in WO 97/04102 (see SEQ ID NO: 2 in WO 97/04102; also shown as SEQ ID NO: 2 of the present application) at a concentration of 33 mg enzyme protein/mL.

The residual antibacterial activity, following incubation at simulated gastric conditions, of lactose oxidase (COX) and vanadium haloperoxidase (HAP) against *Escherichia coli* in a feed slurry background was studied. *E. coli* K12 was inoculated in 10 mL luria broth (LB) and left overnight at 37° C.

Simulated gastric juice composition consisted of 0.001 M HCl, 35 nM NaCl and 1.1 unit pepsin/mL. Different volumes of lactose oxidase and vanadium haloperoxidase was added to 9 mL simulated gastric juice preheated to 40° C. as shown in table 4. Control incubations without gastric challenge were stopped by raising pH to pH 6.5 by addition of 1 mL pH 6.5 citric acid-$Na_2HPO_4$ buffer at t=0 min and prior to addition of enzymes. Gastric challenged samples were stopped by addition of 1 mL pH 6.5 citric acid-$Na_2HPO_4$ buffer at t=15 min.

Chicken feed (30:70 weight ratio blend of soya bean meal and maize meal, 2 g) was weighed and transferred to each incubation together with 100 μL of *E. coli* from the overnight. The incubation with gastric challenged enzymes, *E. coli* and feed was carried out at 40° C. for one hour at 300 rpm. After treatment a dilution range of $10^{-4}$ was carried out in a sterile 0.9% sodium chloride solution (100 μL to 900 μL of sodium chloride in water). The dilutions were dot-spotted on LB agar plates (10 μL per spot) and incubated overnight at 37° C. The colony forming units (CFU) were counted in spots with lower than 30 colonies. The results are given in table 5.

TABLE 4

Amount of lactose oxidase and vanadium haloperoxidase used

| Experiment | Gastric challenge pH 3 | Lactose Oxidase (μL) | Vanadium Haloperoxidase (μL) |
|---|---|---|---|
| 1 | No | 10 | 1 |
| 2 | No | 100 | 10 |
| 3 | No | 100 | 1 |
| 4 | No | 10 | 10 |
| 5 | Yes | 10 | 1 |
| 6 | Yes | 100 | 10 |
| 7 | Yes | 100 | 1 |
| 8 | Yes | 10 | 10 |
| Control 1 | No | — | — |
| Control 2 | Yes | — | — |

TABLE 5

Surviving *E. coli* in contaminated feed when treated with gastric challenged lactose oxidase and vanadium haloperoxidase

| Experiment | CFU | Dilution Factor | Surviving *E. coli* K12 (CFU/mL) |
|---|---|---|---|
| 1 | 13 | $10^4$ | 130.000 |
| 2 | 1 | 10 | 10 |
| 3 | 0 | <10 | <10 |
| 4 | 6 | $10^4$ | 60.000 |
| 5 | 1 | $10^5$ | 100.000 |
| 6 | 0 | <10 | <10 |
| 7 | 3 | 10 | 30 |
| 8 | 6 | $10^4$ | 60.000 |
| Control 1 | 3 | $10^5$ | 300.000 |
| Control 2 | 2 | $10^5$ | 200.000 |

As can be seen in table 5, when feed contaminated with *E. coli* K12 was treated with lactose oxidase and vanadium haloperoxidase, the number of *E. coli* K12 cells in the contaminated feed broth was reduced by more than 10000 times using 100 μL lactose oxidase in combination with 1 or 10 μL vanadium haloperoxidase. Further, even after the enzymes were treated with simulated gastric juice, the lactose oxidase and vanadium haloperoxidase still reduced the number of *E. coli* K12 cells in the contaminated feed broth by more than 10000 times using 100 μL lactose oxidase in combination with 10 μL vanadium haloperoxidase and more than 1000 times when 100 μL lactose oxidase was added in combination with 1 μL vanadium haloperoxidase. This shows that the vanadium haloperoxidase and lactose oxidase are stable under simulated gastric juice challenge and it therefore would be expected that the enzymes will survive passage through the GI tract of an animal.

What is claimed is:

1. A method of controlling the growth of microorganisms in an animal comprising feeding the animal with an antimicrobial composition comprising a lactose oxidase and a vanadium haloperoxidase.

2. The method according to claim 1, wherein the vanadium haloperoxidase and the lactose oxidase are gastric stable.

3. The method according to claim 1, wherein the concentration of lactose oxidase is in the range of 0.01-200 ppm enzyme protein per kg feed.

4. The method according to claim 1, wherein the concentration of vanadium haloperoxidase is in the range of 0.01-200 ppm enzyme protein per kg feed.

5. The method according to claim 1, wherein the antimicrobial composition is a component of animal feed.

6. The method according to claim 1, wherein controlling the growth of microorganism occurs in the gut of the animal.

7. The method according to claim 1, wherein the microorganism is a type of bacterium.

8. The method according to claim 7, wherein the bacterium is selected from the group consisting of *Campylobacter, Clostridium, Escherichia, Listeria,* and *Salmonella*.

9. The method according to claim 1, wherein the composition further comprises one or more additional compounds selected from the group consisting of forage, concentrates, vitamins, minerals, amino acids, enzymes and other feed ingredients.

10. The method according to claim 1, wherein the composition does not contain lactoferrin.

11. The method according to claim 8, wherein said antimicrobial composition kills at least 90% of the number of bacterium.

12. The method according to claim 8, wherein the bacterium is *E. Coli.*

* * * * *

SEQUENCE LISTING

<160> NUMBER OF SEQ ID NOS: 8

<210> SEQ ID NO 1
<211> LENGTH: 495
<212> TYPE: PRT
<213> ORGANISM: Microdochium nivale

<400> SEQUENCE: 1

Met Arg Ser Ala Phe Ile Leu Ala Leu Gly Leu Ile Thr Ala Ser Ala
1               5                   10                  15

Asp Ala Leu Val Thr Arg Gly Ala Ile Glu Ala Cys Leu Ser Ala Ala
                20                  25                  30

Gly Val Pro Ile Asp Ile Pro Gly Thr Ala Asp Tyr Glu Arg Asp Val
            35                  40                  45

Glu Pro Phe Asn Ile Arg Leu Pro Tyr Ile Pro Thr Ala Ile Ala Gln
        50                  55                  60

Thr Gln Thr Thr Ala His Ile Gln Ser Ala Val Gln Cys Ala Lys Lys
65                  70                  75                  80

Leu Asn Leu Lys Val Ser Ala Lys Ser Gly Gly His Ser Tyr Ala Ser
                85                  90                  95

Phe Gly Phe Gly Gly Glu Asn Gly His Leu Met Val Gln Leu Asp Arg
            100                 105                 110

Met Ile Asp Val Ile Ser Tyr Asn Asp Lys Thr Gly Ile Ala His Val

```
            115                 120                 125
Glu Pro Gly Ala Arg Leu Gly His Leu Ala Thr Val Leu Asn Asp Lys
130                 135                 140

Tyr Gly Arg Ala Ile Ser His Gly Thr Cys Pro Gly Val Gly Ile Ser
145                 150                 155                 160

Gly His Phe Ala His Gly Gly Phe Gly Phe Ser Ser His Met His Gly
                    165                 170                 175

Leu Ala Val Asp Ser Val Val Gly Val Thr Val Val Leu Ala Asp Gly
                180                 185                 190

Arg Ile Val Glu Ala Ser Ala Thr Glu Asn Ala Asp Leu Phe Trp Gly
                195                 200                 205

Ile Lys Gly Ala Gly Ser Asn Phe Gly Ile Val Ala Val Trp Lys Leu
210                 215                 220

Ala Thr Phe Pro Ala Pro Lys Val Leu Thr Arg Phe Gly Val Thr Leu
225                 230                 235                 240

Asn Trp Lys Asn Lys Thr Ser Ala Leu Lys Gly Ile Glu Ala Val Glu
                245                 250                 255

Asp Tyr Ala Arg Trp Val Ala Pro Arg Glu Val Asn Phe Arg Ile Gly
                260                 265                 270

Asp Tyr Gly Ala Gly Asn Pro Gly Ile Glu Gly Leu Tyr Tyr Gly Thr
                275                 280                 285

Pro Glu Gln Trp Arg Ala Ala Phe Gln Pro Leu Leu Asp Thr Leu Pro
290                 295                 300

Ala Gly Tyr Val Val Asn Pro Thr Thr Ser Leu Asn Trp Ile Glu Ser
305                 310                 315                 320

Val Leu Ser Tyr Ser Asn Phe Asp His Val Asp Phe Ile Thr Pro Gln
                325                 330                 335

Pro Val Glu Asn Phe Tyr Ala Lys Ser Leu Thr Leu Lys Ser Ile Lys
                340                 345                 350

Gly Asp Ala Val Lys Asn Phe Val Asp Tyr Tyr Phe Asp Val Ser Asn
                355                 360                 365

Lys Val Lys Asp Arg Phe Trp Phe Tyr Gln Leu Asp Val His Gly Gly
370                 375                 380

Lys Asn Ser Gln Val Thr Lys Val Thr Asn Ala Glu Thr Ala Tyr Pro
385                 390                 395                 400

His Arg Asp Lys Leu Trp Leu Ile Gln Phe Tyr Asp Arg Tyr Asp Asn
                405                 410                 415

Asn Gln Thr Tyr Pro Glu Thr Ser Phe Lys Phe Leu Asp Gly Trp Val
                420                 425                 430

Asn Ser Val Thr Lys Ala Leu Pro Lys Ser Asp Trp Gly Met Tyr Ile
                435                 440                 445

Asn Tyr Ala Asp Pro Arg Met Asp Arg Asp Tyr Ala Thr Lys Val Tyr
                450                 455                 460

Tyr Gly Glu Asn Leu Ala Arg Leu Gln Lys Leu Lys Ala Lys Phe Asp
465                 470                 475                 480

Pro Thr Asp Arg Phe Tyr Tyr Pro Gln Ala Val Arg Pro Val Lys
                485                 490                 495
```

<210> SEQ ID NO 2
<211> LENGTH: 600
<212> TYPE: PRT
<213> ORGANISM: Curvularia verruculosa

<400> SEQUENCE: 2

-continued

```
Met Gly Ser Val Thr Pro Ile Pro Leu Pro Thr Ile Asp Glu Pro Glu
1               5                   10                  15

Glu Tyr Asn Asn Asn Tyr Ile Leu Phe Trp Asn Asn Val Gly Leu Glu
            20                  25                  30

Leu Asn Arg Leu Thr His Thr Val Gly Gly Pro Leu Thr Gly Pro Pro
            35                  40                  45

Leu Ser Ala Arg Ala Leu Gly Met Leu His Leu Ala Ile His Asp Ala
50                  55                  60

Tyr Phe Ser Ile Cys Pro Pro Thr Glu Phe Thr Phe Leu Ser Pro
65                  70                  75                  80

Asp Ala Glu Asn Pro Ala Tyr Arg Leu Pro Ser Pro Asn Gly Ala Asp
                85                  90                  95

Asp Ala Arg Gln Ala Val Ala Gly Ala Ala Leu Lys Met Leu Ser Ser
                100                 105                 110

Leu Tyr Met Lys Pro Ala Asp Pro Asn Thr Gly Thr Asn Ile Ser Asp
            115                 120                 125

Asn Ala Tyr Ala Gln Leu Ala Leu Val Leu Glu Arg Ala Val Val Lys
            130                 135                 140

Val Pro Gly Gly Val Asp Arg Glu Ser Val Ser Phe Met Phe Gly Glu
145                 150                 155                 160

Ala Val Ala Asp Val Phe Phe Ala Leu Leu Asn Asp Pro Arg Gly Ala
                165                 170                 175

Ser Gln Glu Gly Tyr Gln Pro Thr Pro Gly Arg Tyr Lys Phe Asp Asp
            180                 185                 190

Glu Pro Thr His Pro Val Val Leu Val Pro Val Asp Pro Asn Asn Pro
            195                 200                 205

Asn Gly Pro Lys Met Pro Phe Arg Gln Tyr His Ala Pro Phe Tyr Gly
210                 215                 220

Met Thr Thr Lys Arg Phe Ala Thr Gln Ser Glu His Ile Leu Ala Asp
225                 230                 235                 240

Pro Pro Gly Leu Arg Ser Asn Ala Asp Glu Thr Ala Glu Tyr Asp Asp
            245                 250                 255

Ser Ile Arg Val Ala Ile Ala Met Gly Gly Ala Gln Asp Leu Asn Ser
            260                 265                 270

Thr Lys Arg Ser Pro Trp Gln Thr Ala Gln Gly Leu Tyr Trp Ala Tyr
            275                 280                 285

Asp Gly Ser Asn Leu Val Gly Thr Pro Pro Arg Phe Tyr Asn Gln Ile
            290                 295                 300

Val Arg Arg Ile Ala Val Thr Tyr Lys Lys Glu Asp Asp Leu Ala Asn
305                 310                 315                 320

Ser Glu Val Asn Asn Ala Asp Phe Ala Arg Leu Phe Ala Leu Val Asn
                325                 330                 335

Val Ala Cys Thr Asp Ala Gly Ile Phe Ser Trp Lys Glu Lys Trp Glu
            340                 345                 350

Phe Glu Phe Trp Arg Pro Leu Ser Gly Val Arg Asp Asp Gly Arg Pro
            355                 360                 365

Asp His Gly Asp Pro Phe Trp Leu Thr Leu Gly Ala Pro Ala Thr Asn
            370                 375                 380

Thr Asn Asp Ile Pro Phe Lys Pro Pro Phe Pro Ala Tyr Pro Ser Gly
385                 390                 395                 400

His Ala Thr Phe Gly Gly Ala Val Phe Gln Met Val Arg Arg Tyr Tyr
                405                 410                 415

Asn Gly Arg Val Gly Thr Trp Lys Asp Asp Glu Pro Asp Asn Ile Ala
```

```
                   420             425             430
Ile Asp Met Met Ile Ser Glu Glu Leu Asn Gly Val Asn Arg Asp Leu
            435             440             445

Arg Gln Pro Tyr Asp Pro Thr Ala Pro Ile Glu Asp Gln Pro Gly Ile
    450             455             460

Val Arg Thr Arg Ile Val Arg His Phe Asp Ser Ala Trp Glu Met Met
465             470             475             480

Phe Glu Asn Ala Ile Ser Arg Ile Phe Leu Gly Val His Trp Arg Phe
            485             490             495

Asp Ala Ala Ala Arg Asp Ile Leu Ile Pro Thr Asn Thr Lys Asp
            500             505             510

Val Tyr Ala Val Asp Ser Asn Gly Ala Thr Val Phe Gln Asn Val Glu
    515             520             525

Asp Val Arg Tyr Ser Thr Lys Gly Thr Arg Glu Gly Arg Glu Gly Leu
    530             535             540

Phe Pro Ile Gly Gly Val Pro Leu Gly Ile Glu Ile Ala Asp Glu Ile
545             550             555             560

Phe Asn Asn Gly Leu Arg Pro Thr Pro Pro Glu Leu Gln Pro Met Pro
            565             570             575

Gln Asp Thr Pro Val Gln Lys Pro Val Gln Gly Met Trp Asp Glu Gln
            580             585             590

Val Pro Leu Val Lys Glu Ala Pro
            595             600

<210> SEQ ID NO 3
<211> LENGTH: 609
<212> TYPE: PRT
<213> ORGANISM: Curvularia inequalis

<400> SEQUENCE: 3

Met Gly Ser Val Thr Pro Ile Pro Leu Pro Lys Ile Asp Glu Pro Glu
1               5                   10                  15

Glu Tyr Asn Thr Asn Tyr Ile Leu Phe Trp Asn His Val Gly Leu Glu
            20                  25                  30

Leu Asn Arg Val Thr His Thr Val Gly Gly Pro Leu Thr Gly Pro Pro
        35                  40                  45

Leu Ser Ala Arg Ala Leu Gly Met Leu His Leu Ala Ile His Asp Ala
    50                  55                  60

Tyr Phe Ser Ile Cys Pro Pro Thr Asp Phe Thr Thr Phe Leu Ser Pro
65                  70                  75                  80

Asp Thr Glu Asn Ala Ala Tyr Arg Leu Pro Ser Pro Asn Gly Ala Asn
            85                  90                  95

Asp Ala Arg Gln Ala Val Ala Gly Ala Ala Leu Lys Met Leu Ser Ser
            100                 105                 110

Leu Tyr Met Lys Pro Val Glu Gln Pro Asn Pro Asn Pro Gly Ala Asn
        115                 120                 125

Ile Ser Asp Asn Ala Tyr Ala Gln Leu Gly Leu Val Leu Asp Arg Ser
    130                 135                 140

Val Leu Glu Ala Pro Gly Gly Val Asp Arg Glu Ser Ala Ser Phe Met
145                 150                 155                 160

Phe Gly Glu Asp Val Ala Asp Val Phe Phe Ala Leu Leu Asn Asp Pro
            165                 170                 175

Arg Gly Ala Ser Gln Glu Gly Tyr His Pro Thr Pro Gly Arg Tyr Lys
            180                 185                 190
```

```
Phe Asp Asp Glu Pro Thr His Pro Val Val Leu Ile Pro Val Asp Pro
            195                 200                 205
Asn Asn Pro Asn Gly Pro Lys Met Pro Phe Arg Gln Tyr His Ala Pro
        210                 215                 220
Phe Tyr Gly Lys Thr Thr Lys Arg Phe Ala Thr Gln Ser Glu His Phe
225                 230                 235                 240
Leu Ala Asp Pro Pro Gly Leu Arg Ser Asn Ala Asp Glu Thr Ala Glu
                245                 250                 255
Tyr Asp Asp Ala Val Arg Val Ala Ile Ala Met Gly Gly Ala Gln Ala
            260                 265                 270
Leu Asn Ser Thr Lys Arg Ser Pro Trp Gln Thr Ala Gln Gly Leu Tyr
        275                 280                 285
Trp Ala Tyr Asp Gly Ser Asn Leu Ile Gly Thr Pro Pro Arg Phe Tyr
    290                 295                 300
Asn Gln Ile Val Arg Arg Ile Ala Val Thr Tyr Lys Lys Glu Glu Asp
305                 310                 315                 320
Leu Ala Asn Ser Glu Val Asn Asn Ala Asp Phe Ala Arg Leu Phe Ala
                325                 330                 335
Leu Val Asp Val Ala Cys Thr Asp Ala Gly Ile Phe Ser Trp Lys Glu
            340                 345                 350
Lys Trp Glu Phe Glu Phe Trp Arg Pro Leu Ser Gly Val Arg Asp Asp
        355                 360                 365
Gly Arg Pro Asp His Gly Asp Pro Phe Trp Leu Thr Leu Gly Ala Pro
    370                 375                 380
Ala Thr Asn Thr Asn Asp Ile Pro Phe Lys Pro Pro Phe Pro Ala Tyr
385                 390                 395                 400
Pro Ser Gly His Ala Thr Phe Gly Gly Ala Val Phe Gln Met Val Arg
                405                 410                 415
Arg Tyr Tyr Asn Gly Arg Val Gly Thr Trp Lys Asp Asp Glu Pro Asp
            420                 425                 430
Asn Ile Ala Ile Asp Met Met Ile Ser Glu Glu Leu Asn Gly Val Asn
        435                 440                 445
Arg Asp Leu Arg Gln Pro Tyr Asp Pro Thr Ala Pro Ile Glu Asp Gln
450                 455                 460
Pro Gly Ile Val Arg Thr Arg Ile Val Arg His Phe Asp Ser Ala Trp
465                 470                 475                 480
Glu Leu Met Phe Glu Asn Ala Ile Ser Arg Ile Phe Leu Gly Val His
                485                 490                 495
Trp Arg Phe Asp Ala Ala Ala Arg Asp Ile Leu Ile Pro Thr Thr
            500                 505                 510
Thr Lys Asp Val Tyr Ala Val Asp Asn Asn Gly Ala Thr Val Phe Gln
        515                 520                 525
Asn Val Glu Asp Ile Arg Tyr Thr Thr Arg Gly Thr Arg Glu Asp Pro
    530                 535                 540
Glu Gly Leu Phe Pro Ile Gly Gly Val Pro Leu Gly Ile Glu Ile Ala
545                 550                 555                 560
Asp Glu Ile Phe Asn Asn Gly Leu Lys Pro Thr Pro Glu Ile Gln
                565                 570                 575
Pro Met Pro Gln Glu Thr Pro Val Gln Lys Pro Val Gly Gln Pro
            580                 585                 590
Val Lys Gly Met Trp Glu Glu Gln Ala Pro Val Val Lys Glu Ala
        595                 600                 605
Pro
```

```
<210> SEQ ID NO 4
<211> LENGTH: 617
<212> TYPE: PRT
<213> ORGANISM: Trichoderma harzianum

<400> SEQUENCE: 4
```

| | | | | | | | | | | | | | | |
|---|---|---|---|---|---|---|---|---|---|---|---|---|---|---|
| Met | Asp | Asn | Val | Asp | Phe | Ala | Glu | Ser | Val | Arg | Thr | Arg | Trp | Ala | Arg |
| 1 | | | | 5 | | | | | 10 | | | | | 15 | |

Arg Leu Ile Arg Glu Lys Val Ala Lys Glu Leu Asn Ile Leu Thr Glu
         20                  25                  30

Arg Leu Gly Glu Val Pro Gly Ile Pro Pro Asn Glu Gly Arg Phe
     35                  40                  45

Leu Gly Gly Gly Tyr Ser His Asp Asn Leu Pro Ser Asp Pro Leu Tyr
         50                  55                  60

Ser Ser Ile Lys Pro Ala Leu Leu Lys Glu Ala Pro Arg Ala Glu Glu
65                  70                  75                  80

Glu Leu Pro Pro Arg Lys Val Cys Ile Val Gly Ala Gly Val Ser Gly
                 85                  90                  95

Leu Tyr Ile Ala Met Ile Leu Asp Asp Leu Lys Ile Pro Asn Leu Thr
            100                 105                 110

Tyr Asp Ile Phe Glu Ser Ser Ser Arg Thr Gly Gly Arg Leu Tyr Thr
            115                 120                 125

His His Phe Thr Asp Ala Lys His Asp Tyr Tyr Asp Ile Gly Ala Met
        130                 135                 140

Arg Tyr Pro Asp Ile Pro Ser Met Lys Arg Thr Phe Asn Leu Phe Lys
145                 150                 155                 160

Arg Thr Lys Met Pro Leu Ile Lys Tyr Tyr Leu Asp Gly Glu Asn Thr
                165                 170                 175

Pro Gln Leu Tyr Asn Asn His Phe Phe Ala Lys Gly Val Ser Asp Pro
            180                 185                 190

Tyr Met Val Ser Val Ala Asn Gly Gly Thr Val Pro Asp Asp Val Val
        195                 200                 205

Asp Ser Val Gly Glu Lys Leu Gln Gln Ala Phe Gly Tyr Tyr Lys Glu
    210                 215                 220

Lys Leu Ala Glu Asp Phe Asp Lys Gly Phe Asp Glu Leu Met Leu Val
225                 230                 235                 240

Asp Asp Met Thr Thr Arg Glu Tyr Leu Lys Arg Gly Pro Lys Gly
                245                 250                 255

Glu Ala Pro Lys Tyr Asp Phe Phe Ala Ile Gln Trp Met Glu Thr Gln
            260                 265                 270

Asn Thr Gly Thr Asn Leu Phe Asp Gln Ala Phe Ser Glu Ser Val Ile
        275                 280                 285

Asp Ser Phe Asp Phe Asp Asn Pro Thr Lys Pro Glu Trp Tyr Cys Ile
    290                 295                 300

Glu Gly Gly Thr Ser Leu Leu Val Asp Ala Met Glu Lys Thr Leu Val
305                 310                 315                 320

His Lys Val Gln Asn Asn Lys Arg Val Asp Ala Ile Ser Ile Asp Leu
                325                 330                 335

Asp Ala Pro Asp Asp Gly Asn Met Ser Val Arg Ile Gly Gly Lys Glu
            340                 345                 350

His Ser Gly Tyr Ser Thr Val Phe Asn Thr Thr Ala Leu Gly Cys Leu
        355                 360                 365

Asp Arg Met Asp Leu Arg Gly Leu Asn Leu His Pro Thr Gln Ala Asp

|  |  |  |  | 370 |  |  |  |  | 375 |  |  |  |  | 380 |  |
| --- | --- | --- | --- | --- | --- | --- | --- | --- | --- | --- | --- | --- | --- | --- | --- |

Ala Ile Arg Cys Leu His Tyr Asp Asn Ser Thr Lys Val Ala Leu Lys
385                 390                 395                 400

Phe Ser Tyr Pro Trp Trp Ile Lys Asp Cys Gly Ile Thr Cys Gly Gly
                405                 410                 415

Ala Ala Ser Thr Asp Leu Pro Leu Arg Thr Cys Val Tyr Pro Ser Tyr
            420                 425                 430

Asn Leu Ala Asp Thr Gly Glu Ala Val Leu Leu Ala Ser Tyr Thr Trp
            435                 440                 445

Ser Gln Asp Ala Thr Arg Ile Gly Ser Leu Val Lys Glu Ala Pro Pro
        450                 455                 460

Gln Pro Pro Lys Glu Asp Glu Leu Val Glu Leu Ile Leu Gln Asn Leu
465                 470                 475                 480

Ala Arg Leu His Ala Glu His Met Thr Tyr Glu Lys Ile Lys Glu Ala
                485                 490                 495

Tyr Thr Gly Val Tyr His Ala Tyr Cys Trp Ala Asn Asp Pro Asn Val
            500                 505                 510

Gly Gly Ala Phe Ala Leu Phe Gly Pro Gly Gln Phe Ser Asn Leu Tyr
            515                 520                 525

Pro Tyr Leu Met Arg Pro Ala Ala Gly Gly Lys Phe His Ile Val Gly
        530                 535                 540

Glu Ala Ser Ser Val His His Ala Trp Ile Ile Gly Ser Leu Glu Ser
545                 550                 555                 560

Ala Tyr Thr Ala Val Tyr Gln Phe Arg Tyr Lys Tyr Lys Met Trp Asp
                565                 570                 575

Tyr Leu Lys Leu Leu Leu Glu Arg Trp Gln Tyr Gly Leu Gln Glu Leu
            580                 585                 590

Glu Thr Gly Lys His Gly Thr Ala His Leu Gln Phe Ile Leu Gly Ser
            595                 600                 605

Leu Pro Lys Glu Tyr Gln Val Lys Ile
        610                 615

<210> SEQ ID NO 5
<211> LENGTH: 605
<212> TYPE: PRT
<213> ORGANISM: Dreschlera hartlebii

<400> SEQUENCE: 5

Met Glu Pro Ile Thr Pro Ile Pro Leu Pro Arg Ile Asp Glu Pro Glu
1               5                   10                  15

Glu Tyr Asn Thr Asn Tyr Val Leu Tyr Trp Asn His Val Gly Leu Glu
            20                  25                  30

Leu Asn Arg Val Thr His Thr Val Gly Gly Pro Gln Thr Gly Pro Pro
        35                  40                  45

Ile Ser Ala Arg Ala Leu Gly Met Leu His Leu Ala Ile His Asp Ala
    50                  55                  60

Tyr Phe Ala Ile Asn Pro Ser Ala Asp Ile Leu Thr Phe Leu Thr Pro
65                  70                  75                  80

Asn Ala Glu Asp Ala Ala Tyr Arg Leu Pro Asp Leu Asn Gly Ala Asp
                85                  90                  95

Asp Ala Arg Gln Ala Val Ala Gly Ala Ser Leu Lys Met Leu Ser Ser
            100                 105                 110

Leu Tyr Met Lys Pro Asp Met Pro Pro Ala Asn Ile Ser Asp Asn Ala
        115                 120                 125

```
Tyr Ala Gln Leu Gly Leu Val Leu Asp Arg Ser Ala Glu Ala Pro
    130                 135                 140

Gly Gly Val Asp Arg Ala Ser Ala Ser Phe Leu Phe Gly Glu Ala Val
145                 150                 155                 160

Ala Asp Val Phe Phe Ala Leu Leu Phe His Ala Pro Gly Ala Ser Gln
                165                 170                 175

Glu Gly Tyr Gln Pro Thr Pro Gly Arg Tyr Arg Phe Asn Asp Glu Pro
            180                 185                 190

Thr His Pro Val Val Leu Val Pro Val Asp Pro Asn Asn Pro Asn Gly
                195                 200                 205

Pro Lys Arg Pro Phe Arg Gln Tyr His Ala Pro Phe Tyr Gly Lys Thr
210                 215                 220

Ala Lys Arg Phe Ala Thr Gln Ser Glu His Ile Leu Ala Asp Pro Pro
225                 230                 235                 240

Gly Leu Arg Ser Ala Thr Asp Glu Ser Thr Glu Tyr Asp Asp Ser Ile
                245                 250                 255

Arg Val Ala Ile Ala Met Gly Gly Ala Thr Gly Leu Asn Ser Thr Lys
                260                 265                 270

Arg Thr Pro Tyr Gln Thr Val Gln Gly Ile Phe Trp Ala Tyr Asp Gly
                275                 280                 285

Ser Asn Leu Ile Gly Thr Pro Pro Arg Gln Tyr Asn Gln Ile Val Arg
        290                 295                 300

Arg Ile Ala Val Thr Tyr Lys Lys Glu Asp Asp Leu Val Asn Ser Glu
305                 310                 315                 320

Val Asn Asn Ala Asp Phe Ala Arg Leu Phe Gly Leu Val Asn Val Ala
                325                 330                 335

Cys Ala Asp Ala Gly Ile Phe Ser Trp Lys Glu Lys Trp Glu Phe Glu
                340                 345                 350

Phe Trp Arg Pro Leu Ser Gly Val Arg Glu Asp Gly Arg Pro Asp His
            355                 360                 365

Gly Asp Pro Phe Trp Leu Thr Leu Gly Ala Pro Ala Thr Asn Thr Asn
370                 375                 380

Asp Ile Pro Phe Lys Pro Pro Phe Pro Ala Tyr Pro Ser Gly His Ala
385                 390                 395                 400

Thr Phe Gly Gly Ala Val Phe Gln Met Val Arg Arg Tyr Tyr Asn Gly
                405                 410                 415

Arg Val Gly Thr Trp Asn Asp Asp Glu Pro Asp Asn Ile Ala Ile Asp
                420                 425                 430

Met Val Val Ser Glu Glu Leu Asn Gly Leu Ser Arg Asp Leu Arg Gln
            435                 440                 445

Arg Tyr Asp Pro Thr Ala Pro Ile Glu Asp Gln Pro Gly Ile Val Arg
450                 455                 460

Thr Arg Val Val Arg His Phe Asn Ser Ala Trp Glu Leu Met Phe Glu
465                 470                 475                 480

Asn Ala Ile Ser Arg Ile Phe Leu Gly Val His Trp Arg Phe Asp Ala
                485                 490                 495

Ala Ala Ala Arg Asp Val Leu Ile Pro Thr Thr Thr Lys Asp Val Tyr
            500                 505                 510

Ala Val Asp Ala Asn Gly Ala Thr Val Phe Gln Asn Val Glu Asp Val
            515                 520                 525

Arg Tyr Ser Thr Lys Gly Thr Arg Glu Gly Cys Glu Gly Leu Phe Pro
    530                 535                 540

Ile Gly Gly Val Pro Leu Gly Ile Glu Ile Ala Asp Glu Ile Phe Thr
```

-continued

```
                545                 550                 555                 560
Ser Gly Leu Arg Pro Thr Pro Glu Ala Gln Pro Ala Pro Gln Glu
                    565                 570                 575

Pro Pro Thr Val Gln Lys Pro Ile His His Lys Ala Ile Met Gly Gly
                580                 585                 590

Gly Glu Glu Ala Phe Val Pro Ala Val Lys Glu Ala Pro
                595                 600                 605

<210> SEQ ID NO 6
<211> LENGTH: 604
<212> TYPE: PRT
<213> ORGANISM: Dendryphiella salina

<400> SEQUENCE: 6

Met Gly Pro Ile Thr Pro Ile Gln Leu Pro Lys Ile Glu Pro Glu
1               5                   10                  15

Glu Tyr Asn Thr Asn Tyr Ile Leu Tyr Trp His His Val Gly Leu Glu
                20                  25                  30

His Asn Arg Val Thr His Ser Val Gly Gly Pro Gln Thr Gly Pro Pro
                35                  40                  45

Ile Ser Ala Arg Ala Leu Gly Met Leu Gln Leu Ala Val His Asp Ala
        50                  55                  60

Tyr Phe Ala Ile Asn Arg Ser Cys Asp Phe Ser Thr Phe Leu Thr Pro
65                  70                  75                  80

Gly Ala Asp Asn Ala Ala Tyr Arg Leu Pro Asn Leu Asn Cys Ala Asn
                85                  90                  95

Asp Ala Arg Gln Ala Val Ala Gly Ala Ser Ile Lys Met Leu Ser Ser
                100                 105                 110

Leu Tyr Ser Lys Pro Val Thr Gln Pro Cys Pro Asn Pro Gly Ala Asn
                115                 120                 125

Ile Ser Asp Asn Ala Tyr Ala Gln Leu Gln Leu Leu His Cys Ser
        130                 135                 140

Ile Glu Asn Ala Pro Gly Gly Val Asp Gln Ala Ser Ala Ser Phe Val
145                 150                 155                 160

Phe Gly Gln Ala Val Ala Lys Val Phe Phe Asn Leu Leu Phe His Pro
                165                 170                 175

Pro Gly Ala Ser Gln Asp Gly Tyr His Pro Thr Pro Gly Arg Tyr Lys
                180                 185                 190

Phe Asp Asp Glu Pro Thr His Pro Val Val Leu Ile Pro Val Asp Pro
                195                 200                 205

Asn Asn Pro Asp Gly Pro Lys Met Pro Phe Arg Gln Tyr His Ala Pro
        210                 215                 220

Phe Tyr Gly Thr Thr Ala Lys Arg Leu Ala Thr Gln Thr Glu His Ile
225                 230                 235                 240

Ile Ala Asp Pro Pro Gly Ile Arg Ser Ala Ala Asp Glu Gly Ala Glu
                245                 250                 255

Tyr Asp Asp Ser Ile Arg Val Ala Ile Ala Met Gly Gly Ala Thr Gly
                260                 265                 270

Leu Ser Ser Thr Lys Arg Ser Pro Tyr Gln Thr Ala Gln Gly Ile Tyr
                275                 280                 285

Trp Ala Tyr Asp Gly Ser Asn Leu Ile Gly Thr Pro Pro Arg Phe Tyr
        290                 295                 300

Asn Gln Ile Val Arg Arg Ile Ala Val Thr Tyr Lys Lys Glu Ala Asp
305                 310                 315                 320
```

```
Leu Ala Thr Ser Glu Val Asn Asn Ala Asp Phe Ala Arg Leu Leu Ala
            325                 330                 335

Leu Val Asn Val Ala Ser Ala Asp Ala Gly Ile Phe Ser Trp Lys Glu
            340                 345                 350

Lys Trp Glu Phe Glu Tyr Trp Arg Pro Leu Ser Gly Val Arg Asp Asp
            355                 360                 365

Gly Arg Pro Asp His Ala Asp Pro Phe Trp Leu Thr Leu Gly Ala Pro
            370                 375                 380

Ala Thr Asn Thr Asn Asp Ile Pro Phe Lys Pro Phe Pro Ala Tyr
385                 390                 395                 400

Pro Ser Gly His Ala Thr Phe Gly Ser Ala Val Phe Gln Met Val Arg
            405                 410                 415

Arg Tyr Tyr Asn Gly Arg Val Gly Thr Trp Lys Lys Asp Glu Pro Asp
            420                 425                 430

Asn Ile Ala Ile Asp Met Met Val Ser Glu Glu Leu Asn Gly Leu Ser
            435                 440                 445

Arg Asp Leu Arg Gln Pro Tyr Asn Pro Thr Ala Pro Ile Thr Asp Gln
450                 455                 460

Pro Gly Val Val Arg Thr Arg Val Val Arg His Phe Ser Ser Ala Trp
465                 470                 475                 480

Glu Leu Met Phe Glu Asn Ala Ile Ser Arg Ile Phe Leu Gly Val His
            485                 490                 495

Trp Arg Phe Asp Ala Ala Ala Ala Arg Asp Ile Leu Ile Pro Thr Thr
            500                 505                 510

Thr Lys Asp Val Tyr Ala Thr Asp Ala Asn Gly Ala Thr Val Phe Gln
            515                 520                 525

Asn Ile Glu Asp Val Arg Tyr Thr Thr Leu Gly Thr Arg Glu Gly His
530                 535                 540

Asp Gly Leu Leu Pro Ile Gly Gly Val Pro Leu Gly Ile Glu Ile Ala
545                 550                 555                 560

Asp Asp Ile Phe Glu Ser Gly Leu Arg Pro Thr Pro Pro Glu Arg Gln
            565                 570                 575

Pro Ile Val Asp Glu Thr Pro Val Gly Gln Lys Ala Lys Gly Met Trp
            580                 585                 590

Glu Gly Glu Gln Ala Pro Leu Met Asp Gln Ala Pro
            595                 600

<210> SEQ ID NO 7
<211> LENGTH: 599
<212> TYPE: PRT
<213> ORGANISM: Phaeotrichoconis crotalariae

<400> SEQUENCE: 7

Met Thr Ser Val Thr Pro Ile Pro Leu Pro Thr Ile Asp Glu Pro Glu
1               5                   10                  15

Glu Tyr Asn Thr Asn Tyr Ile Leu Tyr Trp Asn His Val Gly Leu Gln
            20                  25                  30

Leu Asn Arg Val Thr His Thr Val Gly Gly Pro Leu Thr Gly Pro Pro
            35                  40                  45

Leu Ser Ala Arg Ala Leu Gly Met Leu His Leu Ala Ile His Asp Ala
            50                  55                  60

Tyr Phe Ser Ile Tyr Pro Ser Ala Asp Phe Ser Thr Phe Leu Ser Pro
65                  70                  75                  80

Asp Ala Glu Asn Ala Ala Tyr Arg Leu Pro Ser Pro Asn Gly Ala Asp
            85                  90                  95
```

```
Asp Ala Arg Gln Ala Val Ala Gly Ala Ser Leu Lys Met Leu Ser Ser
                100                 105                 110

Leu Tyr Met Arg Pro Glu Ala Pro Ser Pro Asn Ile Ser Asp Asn Ala
            115                 120                 125

Tyr Ala Gln Leu Gln Leu Ile Leu Asp Gln Ser Ala Val Glu Ala Pro
        130                 135                 140

Gly Gly Val Asp Arg Ala Ser Ala Ser Phe Leu Phe Gly Glu Ala Val
145                 150                 155                 160

Ala Asp Val Phe Phe Ala Leu Leu Asn Asp Pro Arg Gly Ala Ser Gln
                165                 170                 175

Glu Gly Tyr His Pro Thr Pro Gly Arg Tyr Lys Phe Asp Asp Glu Pro
            180                 185                 190

Thr His Pro Val Val Leu Ile Pro Val Asp Pro Asn Asn Pro Ser Gly
        195                 200                 205

Pro Lys Lys Pro Phe Arg Gln Tyr His Ala Pro Phe Tyr Gly Lys Thr
            210                 215                 220

Thr Lys Arg Phe Ala Thr Gln Thr Glu His Val Leu Ala Asp Pro Pro
225                 230                 235                 240

Gly Leu Arg Ser Asn Ala Asp Glu Thr Ala Glu Tyr Asp Asp Ser Ile
                245                 250                 255

Arg Val Ala Ile Ala Met Gly Gly Ala Thr Asp Leu Asn Ser Thr Lys
            260                 265                 270

Arg Ser Pro Trp Gln Thr Ala Gln Gly Leu Phe Trp Ala Tyr Asp Gly
        275                 280                 285

Ser Asn Leu Val Gly Thr Pro Arg Phe Tyr Asn Gln Ile Val Arg
            290                 295                 300

Arg Ile Ala Val Thr Tyr Lys Lys Glu Glu Asp Leu Ala Asn Ser Glu
305                 310                 315                 320

Val Asn Asn Ala Asp Phe Ala Arg Leu Phe Ala Leu Val Asp Val Ala
                325                 330                 335

Cys Thr Asp Ala Gly Ile Phe Ser Trp Lys Glu Lys Trp Glu Phe Glu
            340                 345                 350

Phe Trp Arg Pro Leu Ser Gly Val Arg Asp Asp Gly Arg Pro Asp His
        355                 360                 365

Gly Asp Pro Phe Trp Leu Thr Leu Gly Ala Pro Ala Thr Asn Thr Asn
            370                 375                 380

Asp Ile Pro Phe Lys Pro Pro Phe Pro Ala Tyr Pro Ser Gly His Ala
385                 390                 395                 400

Thr Phe Gly Gly Ala Val Phe Gln Met Val Arg Arg Tyr Tyr Asn Gly
                405                 410                 415

Arg Val Gly Thr Trp Lys Asp Asn Glu Pro Asp Asn Ile Ala Ile Asp
            420                 425                 430

Met Val Ile Ser Glu Glu Leu Asn Gly Leu Ser Arg Asp Leu Arg Gln
        435                 440                 445

Pro Tyr Asp Pro Thr Ala Pro Ile Gln Asp Gln Pro Gly Ile Val Arg
            450                 455                 460

Thr Arg Ile Val Arg His Phe Ser Ser Ala Trp Glu Met Met Phe Glu
465                 470                 475                 480
```

```
Asn Ala Ile Ser Arg Ile Phe Leu Gly Val His Trp Arg Phe Asp Ala
            485                 490                 495

Ala Ala Ala Arg Asp Ile Leu Ile Pro Thr Thr Thr Lys Asp Val Tyr
        500                 505                 510

Ala Val Asp Ala Asn Gly Ala Thr Val Phe Gln Asn Val Glu Asp Val
        515                 520                 525

Arg Tyr Glu Thr Lys Gly Thr Arg Glu Gly Cys Glu Gly Leu Tyr Pro
        530                 535                 540

Ile Gly Gly Val Pro Leu Gly Ile Glu Ile Ala Asn Glu Ile Phe Glu
545                 550                 555                 560

Ser Gly Leu Arg Pro Thr Pro Pro Glu Arg Gln Pro Met Pro Gln Asp
                565                 570                 575

Thr Pro Glu Gln Lys Gly Val Lys Gly Met Trp Glu Gly Glu Gln Ala
            580                 585                 590

Pro Leu Val Arg Glu Ala Pro
        595

<210> SEQ ID NO 8
<211> LENGTH: 614
<212> TYPE: PRT
<213> ORGANISM: Geniculosporium sp.

<400> SEQUENCE: 8

Met Ala Thr Phe Thr Pro Ile Pro Leu Pro Gln Ile Asp Glu Pro Ala
1               5                   10                  15

Glu Tyr Asn Thr Asn Tyr Val Leu Tyr Trp His His Val Gly Leu Glu
            20                  25                  30

Leu Asn Arg Val Thr His Thr Val Gly Gly Pro Gln Thr Gly Pro Pro
        35                  40                  45

Ile Ser Ala Arg Ala Leu Gly Met Leu Gln Leu Ala Val His Asp Ala
    50                  55                  60

Tyr Phe Ala Ile His Pro Ser Ser Ser Phe Leu Thr Phe Leu Thr Ser
65                  70                  75                  80

Gly Ala Asp Asn Pro Ala Tyr Ala Leu Pro Glu Leu Ser Gly Ala Asp
                85                  90                  95

Asp Ala Arg Gln Ala Val Ala Gly Ala Ser Val Thr Met Leu Ser Met
            100                 105                 110

Leu Tyr Met Lys Pro Pro Thr Asn Pro Asn Pro Asn Pro Gly Ala Thr
        115                 120                 125

Ile Ser Asp Asn Ala Tyr Ala Gln Leu Gln Tyr Val Ile Asp Lys Ser
    130                 135                 140

Val Thr Asp Ala Pro Gly Gly Val Asp Ala Ala Ser Ser Ser Phe Asn
145                 150                 155                 160

Phe Gly Lys Ala Val Ala Thr Val Phe Phe Asn Leu Leu Phe His Ala
                165                 170                 175

Pro Gly Ala Ser Gln Ala Gly Tyr His Pro Thr Pro Gly Pro Tyr Lys
            180                 185                 190

Phe Asp Asp Glu Pro Thr His Pro Val Val Leu Val Pro Val Asp Ala
        195                 200                 205

Asn Asn Pro Asp Gly Pro Lys Arg Pro Phe Arg Gln Tyr His Gly Pro
    210                 215                 220
```

```
Phe Tyr Gly Lys Thr Ala Lys Arg Phe Ala Thr Gln Thr Glu His Met
225                 230                 235                 240

Ile Ala Asp Pro Pro Ala Ile Arg Ser Ala Val Gly Glu Gln Ala Glu
            245                 250                 255

Tyr Asp Asp Ser Ile Arg Gln Ile Ile Ala Met Gly Gly Ala Thr Gly
        260                 265                 270

Leu Asn Ser Thr Lys Arg Ser Pro Phe Gln Thr Thr Gln Gly Met Phe
    275                 280                 285

Trp Ala Tyr Asp Gly Ser Asn Leu Val Gly Thr Pro Pro Arg Phe Tyr
290                 295                 300

Asn Gln Ile Val Arg Arg Ile Ala Val Thr Tyr Lys Lys Glu Glu Asp
305                 310                 315                 320

Leu Thr Asn Ser Glu Val Asn Asn Ala Asp Phe Val Arg Leu Leu Ala
                325                 330                 335

Leu Val Asn Val Ala Cys Ala Asp Ala Gly Ile Phe Ser Trp Lys Glu
            340                 345                 350

Lys Trp Glu Phe Glu Phe Trp Arg Pro Leu Ser Gly Val Arg Asp Asp
        355                 360                 365

Asn Phe Arg Asp Pro Asn Arg Pro Asp Arg Gly Asp Pro Phe Trp Leu
370                 375                 380

Thr Leu Gly Ala Pro Ala Thr Asn Thr Asn Asp Ile Pro Phe Lys Pro
385                 390                 395                 400

Pro Phe Pro Ala Tyr Pro Ser Gly His Ala Thr Phe Gly Gly Ala Val
                405                 410                 415

Phe Gln Met Val Arg Arg Tyr Tyr Asn Gly Arg Val Gly Asn Trp Lys
            420                 425                 430

Asp Asp Glu Val Asp Asn Ile Ala Ile Asp Met Met Val Ser Glu Glu
        435                 440                 445

Leu Asn Gly Leu Ser Arg Asp Leu Arg Gln Pro Tyr Asp Pro Lys Ala
    450                 455                 460

Pro Ile Thr Asp Gln Pro Gly Ile Val Arg Thr Arg Val Pro Arg His
465                 470                 475                 480

Phe Ser Ser Val Trp Glu Met Met Phe Glu Asn Ala Ile Ser Arg Ile
                485                 490                 495

Phe Leu Gly Val His Trp Arg Phe Asp Ala Ala Ala Lys Asp Ile
            500                 505                 510

Leu Ile Pro Thr Thr Thr Lys Asp Val Tyr Ala Val Asp Asn Asn Gly
        515                 520                 525

Ala Ser Leu Phe Gln Asn Val Glu Asp Ile Arg Tyr Thr Thr Met Gly
    530                 535                 540

Thr Arg Glu Gly His Asp Gly Leu Leu Pro Ile Gly Gly Val Pro Leu
545                 550                 555                 560

Gly Ile Gly Ile Ala Asn Glu Ile Phe Asp Thr Gly Leu Lys Pro Thr
                565                 570                 575

Pro Pro Glu Lys Gln Pro Val Pro Pro Pro Phe Asn Gln Ser Gly
            580                 585                 590

Pro Thr Lys Glu Met Leu Glu Glu Ala Gly Ser Glu Glu Gln Val Pro
        595                 600                 605

Met Met Asp Val Ala Pro
    610
```